United States Patent [19]

Malinski et al.

[11] Patent Number: 5,603,820
[45] Date of Patent: Feb. 18, 1997

[54] NITRIC OXIDE SENSOR

[75] Inventors: Tadeusz Malinski, Oakland Township, Mich.; David A. Wink, Hagerstown, Md.; Janet Younathan, Rochester, N.Y.; Royce W. Murray, Chapel Hill, N.C.; Melani Sullivan, Rüfenach, Switzerland; Thomas J. Meyer, Chapel Hill, N.C.; Danae D. Christodoulou, Frederick, Md.

[73] Assignees: The United States of America as represented by the Department of Health and Human Services, Washington, D.C.; The University of North Carolina at Chapel Hill, Chapel Hill, N.C.

[21] Appl. No.: 477,620

[22] Filed: Jun. 7, 1995

Related U.S. Application Data

[63] Continuation-in-part of Ser. No. 871,463, Apr. 21, 1992, abandoned, and Ser. No. 918,661, Jul. 22, 1992, abandoned.

[51] Int. Cl.$^6$ ..................................................... G01N 27/26
[52] U.S. Cl. .................... 205/781; 205/782.5; 205/783; 204/415; 204/418; 204/431; 204/432; 204/424; 204/426; 204/282; 204/290 R; 502/163; 502/167
[58] Field of Search .................................... 204/418, 431, 204/432, 424, 426, 282, 290 R, 415; 205/780.5, 781, 782, 782.5, 783; 429/43, 44; 502/167, 163

[56] References Cited

U.S. PATENT DOCUMENTS

| | | | |
|---|---|---|---|
| 4,265,714 | 5/1981 | Nolan et al. | 205/779.5 |
| 4,310,400 | 1/1982 | Mark, Jr. et al. | 204/412 |
| 4,582,589 | 4/1986 | Ushizawa et al. | 204/433 |
| 4,662,996 | 5/1987 | Venkatasetty | 205/781 |
| 4,772,364 | 9/1988 | Dempsey et al. | 205/525 |

(List continued on next page.)

FOREIGN PATENT DOCUMENTS

| | | |
|---|---|---|
| 0235016 | 2/1987 | European Pat. Off. . |
| 57-46154 | 3/1982 | Japan . |
| 58-200157 | 11/1983 | Japan . |
| 60-52759 | 3/1985 | Japan . |
| 1148953 | 6/1989 | Japan . |

(List continued on next page.)

OTHER PUBLICATIONS

Arroyo et al., "Receptor–Mediated Generation Of An EDRF–Like Intermediate In A Neuronal Cell Line Detected By Spin Trapping Techniques," *Biochemical and Biophysical Research Communications*, 170 (3) 1177–1183 (Aug. 16, 1990).

(List continued on next page.)

*Primary Examiner*—Bruce F. Bell
*Attorney, Agent, or Firm*—Leydig, Voit & Mayer, Ltd.

[57] ABSTRACT

An electrode sensor which may be used to specifically and quantitatively measure nitric oxide is provided, as well as a method of preparing and using such an electrode sensor to measure nitric oxide concentration in solution. A nitric oxide (NO) microsensor based on catalytic oxidation of NO comprises a thermally-sharpened carbon fiber with a tip diameter of about 0.5–0.7 μm coated with several layers of p-type semiconducting polymeric porphyrin and cationic exchanger deposited thereon. The microsensor, which can be operated in either the amperometric, voltammetric or coulometric mode utilizing a two or three electrode system, is characterized by a linear response up to about 300 μM, a response time better than 10 msec and a detection limit of about 10 nM. The sensor of the present invention also discriminates against nitrite, the most problematic interferant in NO measurements. The amount of NO released from a single cell can thus be selectively measured in situ by a porphyrinic microsensor of the invention. A larger scale sensor utilizing porphyrin and cationic exchanger deposited on larger fibers or wires, platinum mesh or tin indium oxide layered on glass, can also be employed when measurement of NO concentration in chemical media, tissue or cell culture is desired.

66 Claims, 14 Drawing Sheets

U.S. PATENT DOCUMENTS

| | | | |
|---|---|---|---|
| 4,871,442 | 10/1989 | Yamaguchi et al. | 204/418 |
| 4,886,572 | 12/1989 | Kimura et al. | 216/6 |
| 4,957,615 | 9/1990 | Ushizawa et al. | 204/415 |
| 4,959,132 | 9/1990 | Fedkiw, Jr. | 205/344 |
| 5,116,481 | 5/1992 | Ozawa et al. | 204/290 R |
| 5,173,166 | 12/1992 | Tomantschger et al. | 204/412 |
| 5,227,042 | 7/1993 | Zawodzinski | 204/403 |

FOREIGN PATENT DOCUMENTS

| | | |
|---|---|---|
| 2216447 | 8/1990 | Japan. |
| 3089157 | 4/1991 | Japan. |
| 2173906 | 4/1986 | United Kingdom. |
| 2180653 | 4/1987 | United Kingdom. |
| 2228327 | 8/1990 | United Kingdom. |

OTHER PUBLICATIONS

Bazylinski et al., "Evidence from the Reaction between Trioxodinitrate(II) and $^{13}$NO That Trioxodinitrate(II) Decomposes into Nitrosyl Hydride and Nitrite in Neutral Aqueous Solution," *Inorganic Chemistry*, 24 (25) 4285–4288 (1985) no month available.

Green et al., "Analysis of Nitrate, Nitrite, and [$^{15}$N] Nitrate in Biological Fluids," *Analytical Biochemistry*, 126 131–138 (1982) no month available.

Maragos et al., "Complexes of NO with Nucleophiles as Agents for the Controlled Biological Release of Nitric Oxide. Vasorelaxant Effects," *Journal of Medicinal Chemistry*, 34 (11) 3242–3247 (1991) no month available.

Mulsch et al., "The potent vasodilating and guanylyl cyclase activating dinitrosyl–iron(II) complex is stored in a protein–bound from in vascular tissue and is released by thiols," *Federation of European Biochemical Societies*, 294 (3) 252–256 (Dec. 1991).

Palmer et al., "Nitric oxide release accounts for the biological activity of endothelium–derived relaxing factor," *Nature*, 327 524–526 (Jun. 11, 1987).

Shibuki, "An electrochemical microprobe for detecting nitric oxide release in brain tissue," *Neuroscience Research*, 9 69–76 (1990) no month available.

Shibuki et al., "Endogenous nitric oxide release required for long–term synaptic depression in the cerebellum," *Nature*, 349 326–328 (Jan. 24, 1991).

Wennmalm et al., "Detection of Endothelial–Derived Relaxing Factor in Human Plasma in the Basal State and following Ischemia Using Electron Paramagnetic Resonance Spectrometry," *Analytical Biochemistry*, 187 359–363 no month available.

Wink et al., "Unusual Spin–Trap Chemistry for the Reaction of Hydroxyl Radical With The Carcinogen N–Nitrosodimethylamine," *Radiat. Phys. Chem.*, 38 (5) 467–472 (1991) no month available.

Baily et al., "Carbon–Fiber Ultramicroelectrodes Modified with Conductive Polymeric Tetrakis (3–methoxy–4–hydroxphenyl) porphyrin for Determination of Nickel in Single Biological Cells," *Anal. Chem*, 63, 395–398 (1991) no month available.

Bennett et al., "Conductive Polymeric Porphyrin Films: Application in the Electrocatalytic Oxidation of Hydrazine," *Chem. Materials*, 3, 490–495 (1991) no month available.

Courthaudon, "Nitrogen–Specific Gas Chromatography Detection Based on Chemiluminescence," *LC–GC*, 9, 732–735 (1991) no month available.

Freeman, "Fiber Optic Sensor for NO," *Anal. Chem. Acta*, 256, 269–275 (1992) no month available.

Freiman et al., "Antherosclerosis Impairs Endothelium–Dependent Vascular Relaxation to Acetylcholine and Thrombin in Primates," *Circ. Res*, 58, 783–789 (1986) no month available.

Furchgott, "Mechanism of Vasodilation," Vanhoutte, P. M.; Raven, New York; IV, 401–414, (1988) no month available.

Furchgott et al., "The Obligatory Role of Endothelial Cells in the Relaxation of Arterial Smooth Muscle by Acetylcholine," *Nature*, 288, 373–376 (1980) no month available.

Ignaro et al., "Endothelium–derived Relaxing Factor Produced and released from Artery and Vein is Nitric Oxide," *PNAS (USA)*, 84, 9265–9269 (1987) no month available.

Malinski et al., "Conductive Polymeric Tetrakis (3–methoxy–4–hydroxyphenyl) porphyrin Film Electrode for Trace Determination of Nickel," *Anal Chem.*, 62, 909–914 (1990) no month available.

Malinski et al., "Determination of Nickel Accumulation in Single Biological Cells using porphyrinic Microsensors," *Anal. Chem. Acta.*, 249, 35–41 (1991) no month available.

Malinski et al., "Characterization of Conductive Polymeric Nickel (II) Tetrakis (3–methoxy–4–hydroxy–phenyl) Porphyrin as an Ano Material for Electrcaalysis," *J. Electrochem. Soc.*, 138 2008–2015 (1991) no month available.

Malinski et al., "Conductive Polymeric Porphyrins –Characterization and Application for Amperometric Sensors," Reprinted from Proceedings of the Twelfth Annual International Conference of the IEEE Engineering in Medicine and Biology, 12, 1691–1692 (1990) no month available.

Marletta, "Nitric Oxide: Biosynthesis and Biological Significance," *Trends Biochem. Sci.*, 14, 488–492 (1989) no month available.

Moncada et al., "Nitric Oxide: Physiology, Pathophysiology, and Pharmacology," *Pharmacol. Rev.*, 43, 109–142 (1991) no month available.

Rosenthal et al., "Macrovascular Endothelial Cells from Porcine Aorta," *Cell Culture Techniques in Heart and Vessel Research* (ed. Piper H. M.) Spring–Verlag, New York, 117–139 (1990) no month available.

Schuman et al., "A Requirement for the intercellular Messenger Nitric Oxide in Long–term Potentiation," *Science*, 254, 1503–1506 (1991) no month available.

Schuman et al., "A requirement for the Intercellular Messenger Nitric Oxide in Long–term Potentiation," *Science*, 254, 1503–1506 (1991) no month available.

Snyder et al., "Biological Roles of Nitric Oxide," *Scientific Am.*, 266, 68–77 (1992) no month available.

Sung et al., "Direct Measurement of Nitric Oxide in Headspace Gas Produced by a Chicken Macrophage Cell Line in a Closed Culture System," *Biochem. and Biophys. Res. Comm.*, 184, 36–42 (1992) no month available.

Vanbethaysen et al., "Reperfusion after Acute Coronary Occlusion in Dogs Impairs Endothelium–dependent Relaxation to Acetylcholine and Augments Contractile Reactivity In Vitro," *J. Clin Invest*, 79, 265–274 (1987) no month available.

Wei et al., "Superoxide Generation and Reversal of Acetylcholine–Induced Cerebral Arteriolar Dilation after Acute Hypertension," *Cir. Res.*, 57, 781–787 (1985) no month available.

Downes et al., *Analyst*, 101, 742–748 (1978) no month available.

Matusiewicz et al., "Electrochemical Preconcentration of Metals Using Mercury Film Electrodes Followed by Electrothermal Vaporization into an Inductively Coupled Plasma and determination by Atomic Emission Spectrometry," *Anal. Chem.*, 57, 2264–2269 (1987) no month available.

Kadish et al., "Electrchemical Characterization of Six–Coordinate Nitrosyl –Bonded Iron–Phenylporphyrins," *Inorg. Chem.*, 23, 2372–2373 (1984) no month available.

Kelly et al., "Electron–Transfer and Ligand–Addition Reactions of (TTP)Mn(NO) and (TTP)Co(NO) in Nonaqueous Media," *Inorg. Chem.*, 23, 1451–1458 (1984) no month available.

Kelly et al., "Electron–Transfer and Ligand–Addition Reactions of $(TTP)CrClO_4$ and (TTP)Cr(NO) in Nonaqueous Media," *Inorg. Chem.*, 23, 679–687 (1984) no month available.

NITRIC OXIDE SENSOR

This is a continuation in part of Ser. No. 07/871,463 filed Apr. 21, 1992, now abandoned and of Ser. No. 07/918,661 Jul. 22, 1992, now abandoned.

FIELD OF THE INVENTION

The present invention generally relates to sensors and sensing techniques which can selectively and quantitatively detect NO in solution in both biological and chemical media. More specifically, the present invention relates to NO sensors which utilize conductive catalytic materials deposited on microfibers or other supports to monitor the presence or release of NO using amperonmetric, voltammetric or coulometric methods. In addition, this invention relates to a method of manufacturing the electrode sensor and a method of using the electrode sensor to detect and/or measure nitric oxide in a sample.

BACKGROUND OF THE INVENTION

Nitric Oxide (NO) has recently been shown to be a key bioregulatory molecule in a number of physiological processes. For example, NO plays a major role in the biological activity of endothelium derived relaxing factor (EDRF), abnormalities in which are associated with acute hypertension, diabetes, ischaemia and atherosclerosis. NO is also considered a retrograde messenger in the central nervous system, appears to be involved in the regulation of macrophage cytotoxic activity and platelet aggregation inhibition, and has been implicated in endotoxic shock and genetic mutations. In addition, a number of drugs and other xenobiotics are metabolized to produce NO as either the effector molecule or as a harmful metabolite. Many tissues in the body endogenously release NO in different amounts but the actual amount released are very difficult to quantify. In addition, many diseases, such as ischemia reperfusion injury, which include deamination-related genetic diseases like deamination of cytosine to thymine, cancer, and male impotence, have been suggested to be caused by defects in the production and/or regulation of NO. See e.g. Furchgott, R. F. et al., *Nature* 288:373–376 (1980); Palmer, R. M. et al., *Nature* 327:524–526 (1987); Furchgott, R. F., "Mechanism of Vasodilation", IV:401–414 (ed. Vanhoutte, P. M.) (Raven, N.Y.) (1988); Ignaro, L. J. et al., PNAS (USA) 84:9265–9269 (1987); Wel, E. P. et al., *Cir. Res.* 57:781–787 (1985); Piper, G. M. et al., *J. Am. J. Physiol.* 24:4825–4833 (1988); Vanbethuysen, K. M. et al., *J. Clin. Invest.* 79:265–274 (1987); Frelman, P. C. et al., *Circ. Res.* 58:783–789 (1986); and Schuman, E. M. et al., *Science* 254:1503 (1991).

The importance of the bioregulation effected by NO is further evidenced by the recent rash of pharmaceutical companies designing drugs around NO. It is hoped that drugs can be developed to control blood pressure, prevent atherosclerosis, treat migraine headaches and impotence, prevent deaths from septic shock, and help protect brain cells threatened by degenerative diseases and strokes.

Accordingly, the ability to specifically and quantitatively measure NO concentrations in solutions, particularly aqueous solutions of biological media, both in vitro and in vivo, and chemical media would be highly advantageous. The ability to measure the concentration of NO by a nondestructive method is an important requirement for further investigation of the mode of action of NO as a key bioregulatory molecule and for the development of therapeutic applications of NO-releasing compounds.

Several different methods have been employed in the past to measure NO concentration in aqueous solution. An automated system analyzes nitrate by reduction with a high-pressure cadmium column to determine amounts of nitrate and/or nitrite in urine, saliva, deproteinized plasma, gastric juice, and milk samples (Green et al., Analytical Biochemistry 126: 131–138. 1982.). The lower limit of detection of the method is said to be 1.0 nmol $NO_3^-$ or $NO_2^-$/ml. The system reportedly allows quantitative reduction of nitrate and automatically eliminates interference from other compounds normally present in biological fluids. Most samples may be prepared by simple dilution with distilled water, and 30 samples reportedly may be analyzed in an hour. The disadvantage of such a technique in measuring NO is that it does so indirectly, by measuring NO byproducts, which also can be generated from other sources. Accordingly, such a method is not very accurate in determining NO concentration.

Another method quantitatively analyzes nitrite, an oxidation product of NO, in human plasma to determine NO concentration (Wennmalm et al., Analyt. Biochem. 187:359–363. 1990). Dithionite is used to treat the samples of human plasma to convert nitrite to nitric oxide, with the treated samples being passed over bovine homoglobin columns. NO is allowed to bind the hemoglobin in columns of bovine hemoglobin covalently bound to agarose. An excess of dithionite is used to ensure that the hemoglobin is reduced to a ferrous, nonoxygenated state. The NO bound to the hemoglobin forms a complex on the column, and the column is then subjected to electron paramagnetic resonance spectrometry, i.e., the column is subjected to a magnetic field and microwave radiation to obtain a characteristic electron paramagnetic resonance spectrum. This method suffers from the same disadvantages as the previously described method. NO concentration is determined indirectly, through the measurement of nitrite. Also, the NO is modified by binding to hemoglobin covalently bound to agarose.

Other methods employed to quantitate NO include chemiluminescence, mass spectrometry (Bazylinski et al., Inorg. Chem. 24: 4285–4288. 1985), and ultraviolet-visible light spectral changes. In one procedure utilizing chemiluminescence, NO has been quantified by chemiluminescence resulting from the product of NO and ozone (Palmer et al., Nature 327: 524–526. 1987; Maragos et al., J. Med. Chem. 34: 3242–3247. 1991). This method also involves modification of NO, in this case by reaction with ozone. In a procedure employing ultraviolet and visible light, spectral changes have been monitored for the conversion of oxyhemoglobin to methemoglobin by NO as an indication of NO concentration (Haussman et al.). NO is modified in this method by reaction with oxyhemoglobin. Accordingly, neither one of these methods enables the measurement of NO directly.

Solution methods have been also used to measure NO but seem to lack specificity for NO or reliable quantitation. The use of 3,5-dibromo-4-nitrosobenzene sulphonate (DBNBS) as a spin trap in an electron spin resonance technique to detect NO in a biological system has been reported (Arroyo et al., Biophys. Res. Comm. 170: 1177–1183. 1990). This method, consequently, involves reaction of NO with modified spin traps. Subsequently, it was demonstrated that the obtained signal may result from simple oxidation of the spin trap, which raises the issue of how specific the spin trap is for NO (Wink et al., Radiat. Phys. Chem. 38: 467–472. 1991). The use of $Fe^{2+}$ (dithiolate) to trap NO as the nitrosyl also has been used in a spin resonance technique (Mulsch et al., FEBS Letter 294: 252–256. 1991.); however, this technique is not suitable for quantitation due to a lack of biological stability, i.e., the resulting nitrosyl has a half-life of only about 30 seconds in biological systems. Further, it is evident that this method involves the modification of NO by formation of a complex with iron. The iron complex is metabolized, i.e., destroyed, during the process. Also, this method suffers from nitrite interference.

More recently, a modified oxygen electrode has been used to detect NO (Shibuki et al., Neuroscience Res. 9: 69–76. 1990.; Nature 349: 326–328. 1991.). The electrochemical microprobe was developed to detect the release of NO in brain tissue. The output current of the probe was found to correlate linearly with the concentration of NO at the tip. The sensitivity of the probe was reportedly between 3.5 and 106 pA/μM change in NO concentration. However, the validity of this technique has been questioned due to the small current that has been observed (<0.5 pA) and the lack of use of standards at submicromolor concentrations of NO. In addition, the technique measures NO by its oxidation to nitrite, and those who developed the modified oxygen electrode claim that NO is spontaneously released from sodium nitroprusside and that the release is accurately measured by the electrode. This contradicts what has been shown previously by others, i.e., that sodium nitroprusside does not spontaneously release NO in buffer (Kruszyna et al., Toxicol. Appl. Pharmacol. 91: 429–438. 1987.; Wilcox et al., Chem. Res. Toxicol. 3: 71–76. 1990.), which raises the issue of specificity of this method. Further, this electrode has a relatively large diameter (0.25 mm), a slow response time and a narrow concentration range (1–3 μM). Although this method is advantageous in that it discriminates against the $NO_2^-$ produced in the outer solution of the electrode, it is not selective for NO in the presence of any $NO_2^-$ produced in the electrode inner solution.

Although the above-described methods can be used to measure NO in biological or chemical media, they are not sufficiently sensitive nor specific to provide a direct and accurate quantitative measurement of NO, particularly at low NO concentrations. Furthermore, none of the methods or sensors employed to date can rapidly and selectively measure NO release by the cell in situ in the presence of oxygen and/or $NO_2^-$. Development of this methodology is crucial in order to evaluate endogenous NO release, distribution and reactivity on molecular level in biological systems.

Thus, there exists a need for a sensitive and selective sensor for direct quantitive measurements of NO. An optimal sensor for monitoring NO release should be sturdy and capable of sufficient miniaturization for in situ measurement in a single cell. The sensor should also be sensitive enough to produce an adequate signal to be observable at the low levels of NO secreted in biological environments. Due to the variation in the amount of NO secreted by different types of cells (e.g. from nanomoles/$10^6$ cells in macrophages to picomoles in endothelial cells), the signal produced by the sensor should also change linearly over a wide range of concentrations. See Marietta, M. A., *Trends Biochem. Sci.* 14:488–492 (1989). The short half-life of NO in biological systems, on the order of about 3–50 seconds, also mandates a fast response time. See Moncada, S. et al., *Pharmacol. Rev.* 43:109–142 (1991). The NO sensor and method of the present invention exhibit these desirable characteristics.

SUMMARY OF THE INVENTION

The NO sensor and method of the present invention provide a direct and accurate measurement of NO in biological media, both in vitro and in vivo and chemical media. A sensor of the present invention generally comprises an electrode having a catalytic material capable of catalyzing oxidation of NO coated with a cationic exchanger. The sensor provides a direct measurement of NO through the redox reaction of $NO \rightarrow NO^+ + e^-$ and is selective for NO through the discrimination of the cationic exchanger against nitrite ($NO_2^-$). Although the sensor can be fabricated on any scale, it can be miniaturized to provide a microsensor which can accurately measure NO in situ at the cell level. This invention also provides a method of measuring NO concentration, which utilizes the present inventive electrode, and a method of manufacturing the electrode.

In one preferred embodiment of the invention, the amount of NO released from a single cell can be selectively measured in situ by a microsensor with a response time better than about 10 msec. The microsensor comprises a thermally-sharpened conductive carbon fiber with a tip diameter of about 0.5–0.7 μm covered with several layers of polymeric porphyrin capable of catalyzing NO oxidation with a cationic exchanger deposited thereon. Using either a two or three electrode arrangement, the microsensor can be operated in either the amperometric, voltammetric or coulometric mode. The microsensor is characterized by a linear response up to about 300 μM and a detection limit of about 10 nM NO concentration, which allows detection of NO release at the levels present in a single biological cell. The sensor also discriminates against $NO_2^-$, the most problematic interferant with current NO sensing techniques.

In other embodiments of the present invention, larger scale NO sensors are used to measure NO concentrations in chemical media, cell culture, extracellular fluids and tissue, rather than in single cells. For example, a carbon electrode with a larger tip diameter, platinum mesh or a tin indium oxide layered plate is coated with a conductive catalytic polymeric porphyrin and a cationic exchanger. A linear response and low detection limits similar to the No microsensor are observed.

The present invention further provides a means of monitoring NO production or inhibition effected by drugs and in the design of drugs for the treatment of diseases related to defects in NO regulation and/or production, both in vitro and in vivo. The ability to monitor NO production or inhibition is also useful as a means of detecting and quantifying defects in NO regulation and/or production, both in vitro and in vivo, which result from disease, injury, and mutation.

The present invention additionally provides a means of monitoring pollution of which NO is a component.

Other features and advantages of the present invention will become apparent from the following description and appended claims, taken in conjunction with the accompanying drawings.

BRIEF DESCRIPTION OF THE DRAWINGS

FIG. 2 is a differential pulse voltammogram of current (i, nA) versus potential (V) for 10 μM, 20 μM, and 40 μM NO in 0.1M phosphate buffer, pH=7.4, at room temperature, prepared using a glassy carbon electrode (GCE)/Ni(II) TMPP electrode coated with Nafion® (Aldrich Chemical Co., Milwaukee, Wis.) at an Epa=0.7 V vs. a standard calomel electrode (SCE).

FIG. 3 is a graph of current (i, nA) versus NO concentration (μM) prepared using a GCE/Ni(II) TMPP electrode coated with 4 μl Nafion®, which shows the NO response of NO solutions of varying NO concentration in 0.1M phosphate buffer, pH=7.4, prepared from a saturated solution of NO at room temperature.

DETAILED DESCRIPTION OF THE PREFERRED EMBODIMENTS

Figure 1A:
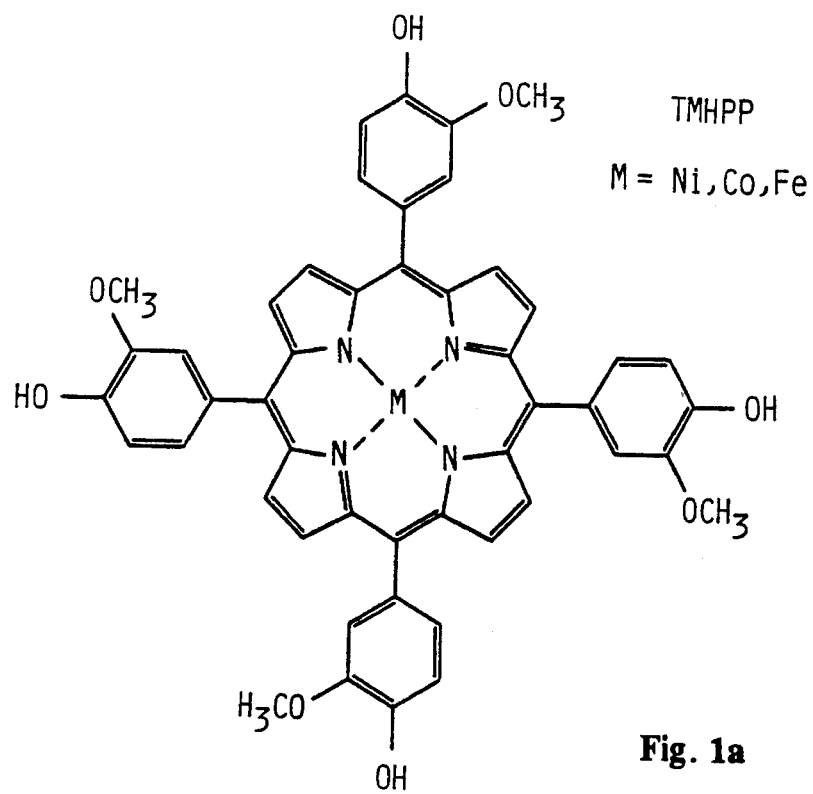
FIGS. 1a and b depict preferred monomeric porphyrin structures used in sensors of the present invention.
Figure 1B:
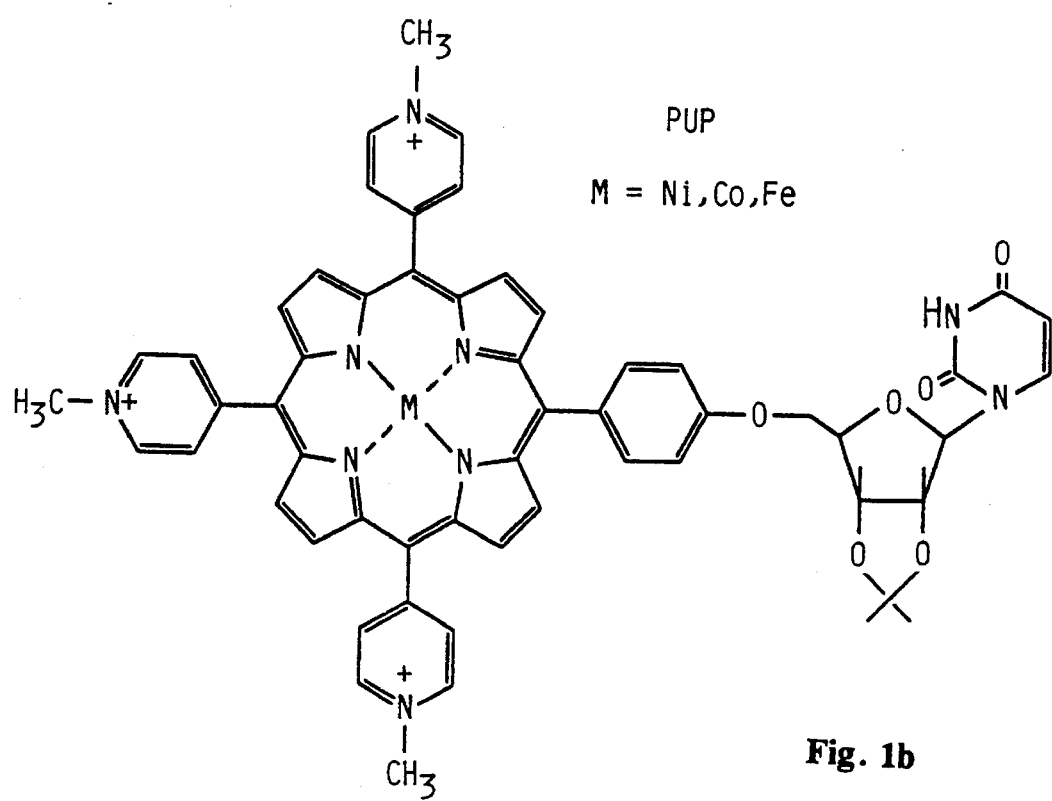
FIG. 1c is a drawing of the structure of tetramethylpyridylporphyrin (TMPP).
FIG. 1d is a drawing of the structure of protoporphyrin IX dimethyl ester (DME).

The present invention provides an electrode sensor that detects NO, as well as methods of making and using such an electrode sensor. The electrode may be used to specifically and quantitatively measure NO in a variety of solutions, particularly aqueous solutions of biological media, both in vitro and invivo, and chemical media.

Specifically, the nitric oxide-specific electrode sensor comprises an electrically conductive substrate, whose amperometric response is substantially unaffected by the presence of nitric oxide, and an adherent and substantially uniform electrochemically active polymeric coating which interacts with NO in such a manner so as to cause a change in the redox potential of NO and the electrode sensor.

The electrically conductive substrate is preferably electrically conductive carbon, indium tin oxide, iridium oxide, nickel, platinum, silver, or gold. The electrically conductive substrate is preferably electrically conductive carbon, such as basal plane carbon, pyrolytic graphite (BPG), or glassy carbon. The preferred electrically conductive substrate will depend in part on whether oxidation or reduction at the electrode sensor will be taking place during use. For example, a nobel metal such as platinum or gold could evolve hydrogen from water reduction which could adversely affect the polymer film(s) on the substrate. The electrically conductive substrate is most preferably glassy carbon.

The basic strategy used in the design of a preferred embodiment of the NO sensor is based on catalytic oxidation of NO which uses a specific potential unique to $NO \rightarrow NO^+ =E^-$. The normal oxidation potential for NO is about 1.0 V vs SCE on a standard platinum electrode, which potential can be lowered with various materials capable of catalytically oxidizing NO. The current or charge generated thereby is high enough to be used as an analytical signal in microsystem.

In accordance with the principles of the present invention, a working electrode of a sensor of the present comprise a conductive solid support with a catalytic surface for NO oxidation. A catalytic surface on a conductive support can be provided using several approaches. For example a conductive catalytic material capable of catalyzing NO oxidation can be layered on a conductive solid support; the conductive catalytic material can be layered on a conductive material coated on a conductive or nonconductive base material; or the conductive catalytic material can itself comprise the conductive support. The third approach can be accomplished by fashioning the electrode directly from the conductive catalytic material or by incorporating or doping a catalyst into the support material. A working electrode of a sensor of the described embodiment of this invention preferably comprises a solid conductive support coated with one or more layers of a conductive material capable of catalyzing oxidation of NO, hereinafter referred to as catalytic material.

It will be appreciated that several types of catalytic materials can be used in a sensor of the present invention, as long as the catalytic material exhibits electronic, ionic or redox conductivity or semiconductivity, collectively referred to herein as conductivity. The change in the observed current drawn through the electrode sensor at a particular potential can be correlated to the concentration of NO in the sample being evaluated. Such materials include, but are not limited to, polymeric porphyrins and polyphthalocyanines. The above-mentioned materials can contain central metals, preferably transition or amphoteric metals. The metallized or doped polymer may contain any suitable metal which will interact with NO, such as the transition or amphoteric metals and preferably nickel, cobalt, or iron. Polymers which can also be used but require doping include, for example, polyvinylmetallocenes (e.g. ferrocene), polyacetylene doped with different metal redox centers and polypyrraline doped with different redox centers such as, e.g. methyl viologen. Polymeric substituted glyoximes may also be employed.

Figure 1C:
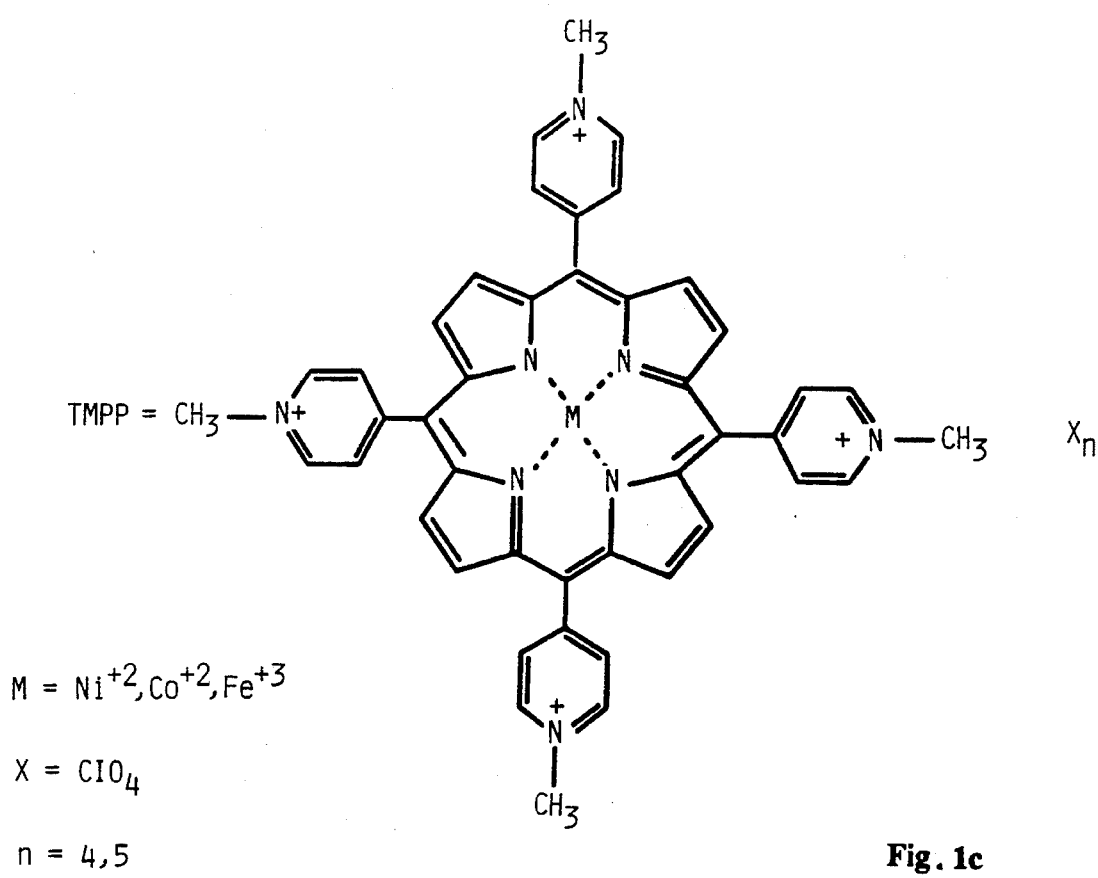
Figure 1D:
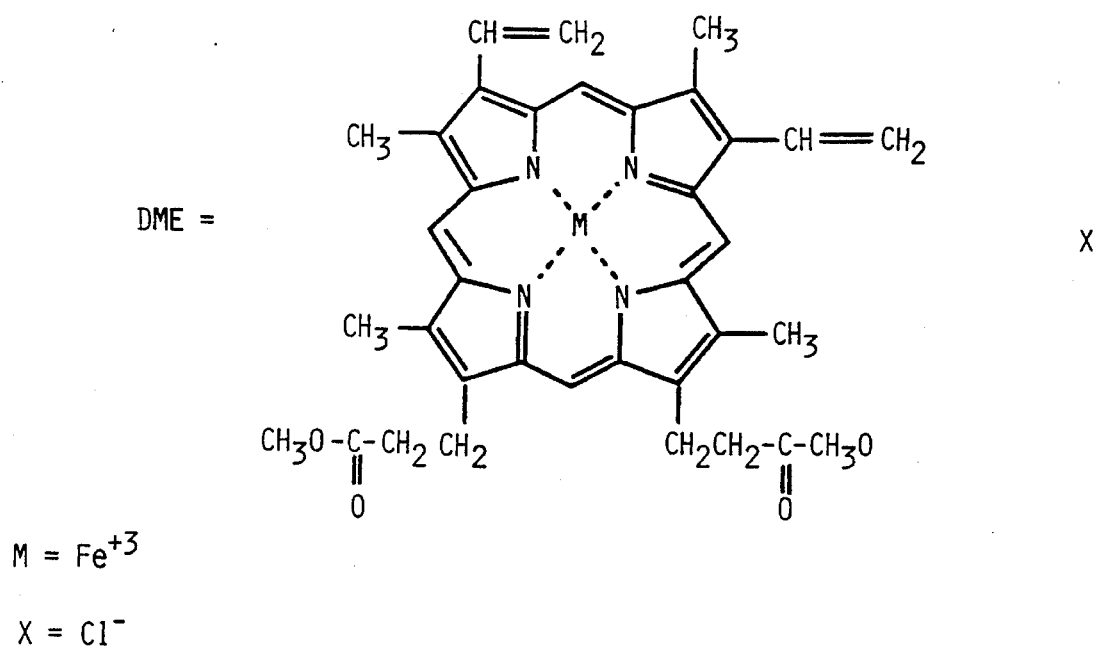

Preferred catalytic conductive materials for a sensor of the present invention are polymeric metalloporphyrins or metallized polyphthalocyanine, most preferably polymeric metalloporphyrins, which are organic p-type semiconductors with relatively high conductivity and which can be successfully deposited on a supporting conductive material. The metallized polymeric porphyrin compounds should not form metal-oxo bridges (M-O-M) with the substrate. Polymeric metalloporphyins have been shown to have high catalytic effect for the electrochemical oxidation of several small organic and inorganic molecules. Bennett, J. E. et al., *Chem. Materials* 3:490–495 (1991). Polymeric porphyrins polymerized and copolymerized from monomeric porphyrins N,N'-di(5-p-phenylene-10,15,20-tri(3-methoxy-4-hydroxyphenyl)porphyrin,1,10,-phenantroline-4,7-diamine, and 5-p-(pyrole-1-yl) phenylene-10,15,20-tri-(3-methoxy-4-hydroxyphenyl)porphyrin with Fe, Mn, Co and Ni as central metals are more preferred given their high catalytic effect for selective electrochemical oxidation of NO. Even more preferred compounds include tetrakis(3-methoxy-4-hydroxyphenyl) porphyrin (TMHPP) and meso-5'-0-p-phenylene-2',3'-0-isopropylidene uridine-tri(n-methyl-4-pyridinium)porphyrin (PUP), shown in FIGS. 1a and b. The electrochemically active polymeric coating is also preferably comprised of the metallized polymeric porphyrin compounds of tetramethyl pyridine pyrrole and dimethyl ester porphyrin, especially tetramethyl pyridine pyrrole (TMPP) and dimethyl ester porphyrin (DME) metallized with nickel, cobalt, and iron. These most preferred metallized porphyrin compounds of TMPP and DME are respectively depicted in FIG. 1c and 1d, wherein M is any suitable metal ion, such as $Ni^{2+}$, $Co^{2+}$, or $Fe^{3+}$, X is a suitable anion to render the compound neutral, such as $ClO_4^-$ in the case of TMPP and $Cl^-$ in the case of DME, and n is an integer sufficient to render the compound neutral, such as 4 in the case of $Ni^{2+}$ and $Co^{2+}$ TMPP, 5 in the case of $Fe^{3+}$ TMPP, and 1 in the case of $Fe^{3+}$ DME (not shown). The particular TMPP and DME compounds utilized in some of the examples herein are depicted in FIG. 1c and 1d.

The electrochemically active polymeric coating should be adherent to and substantially uniform over the substrate. While the polymeric coating may be of any suitable thickness, it is preferably between about 0.01 μm and about 50 μm in thickness.

It will be appreciated by one who is skilled in the art that electrochemically active polymeric coatings will differ in affinity for various substrates. The electrochemically active polymeric coating as used in the present inventive electrode sensor preferably has a high affinity for the particular substrate being used.

In order to discriminate against interfering ions and compounds, particularly $NO_2^-$, the porphyrinic catalysts used in the present invention are also preferably covered with a thin layer of a cationic exchanger or gas-permeable membrane to prevent anion diffusion to the catalytic surface. The gas-permeable membrane coating may be of any suitable material, preferably a perfluorinated compound such as Nafion® (Aldrich Chemical Co., Milwaukee, Wis.). Suitable cationic exchangers include AQ55D available from Kodak and the stated Nafion®. Nafion®, which is used in the Specific Examples, is a negatively charged cationic exchange polymer which prevents diffusion of anions like $NO_2^-$ to the electroactive surface of the polymeric porphyrin, but is highly permeable to NO. The layer of cationic exchanger or gas-permeable membrane coating deposited onto the surface of the electrode sensor may be of any suitable thickness, preferably about 0.5–50 μm. The resulting membrane-coated NO electrode sensor is more selective to NO than an uncoated electrode due to the membrane exclusion of interfering species such as nitrite.

The thin layer of polymeric porphyrin film can be electrochemically deposited, as described in detail below, on any solid conductive support. As previously discussed, a conductive support can comprise a material that in itself is conductive or a conductive or nonconductive base material coated with a conductive material. Conductive materials which do not need to be coated with additional conductive materials are preferred. It will also be appreciated that, although the catalytic component of the invention is preferably layered on a conductive support the conductive catalytic material can also comprise the conductive support. One who is skilled in the art will appreciate that the sensor of the present invention may vary in size, according to the particular application at hand. Therefore, the present inventive sensors may range from macroelectrode sensors to microelectrode sensors and nanoelectrode sensors, utilizing, for example, the edges of carbon films and suitable metal films, as well as carbon fibers. Such submicron size electrodes are more suitable for intracellular and in vivo use. Conductive support materials particularly suitable for smaller scale sensors of the invention include carbon fibers, and gold or platinum wire. Due to their mechanical properties as well as the possibility for controlled miniaturization, carbon fibers are preferable support materials for microsensors in single cell applications. See e.g. Malinski, T. et al. *Anal. Chem. Acta.* 249:35–41 (1991); Bailey, F. et al., *Anal. Chem.* 63:395–398 (1991).

It will be appreciated that the dimension of the sensor of the invention can be varied to produce virtually any size sensor, including microsensors with a tip diameter of about 1 μm or less and macrosensors, including fibers with a larger tip diameter (e.g. about 1–10 mm) and metallic mesh and conductive layered plates. Thus, while Specific Examples IV–VII describe the production and use of a microsensor for use in small environments such as single cells or synapses, the same techniques can be applied to a larger support, such as described in Specific Examples I–III and VIII, to produce convenient macrosensors for tissue, cell culture or chemical media studies.

The present inventive nitric oxide-specific electrode sensors may be prepared in any suitable manner. An adherent and substantially uniform coating of an electrochemically active polymer as previously described is formed on a surface of an electrically conductive substrate as also previously described, by any suitable means, preferably by electrolytic polymerization.

The precursor (e.g., monomer, dimer, or oligomer) used to form the electrochemically active polymeric coating can be electrolytically polymerized onto a surface of the electrically conductive substrate by immersing the substrate in an appropriate electrolyte solution containing the precursor in combination with a supporting electrolyte. The electrolyte solution will typically additionally contain a suitable solvent. Examples of solvents that may be used in the electrolyte solution include acetonitrile, methanol, dimethyl formamide, dimethyl sulfoxide, propylene carbonate, and the like. The supporting electrolyte preferably is a perchlorate, sulfuric acid, phosphoric acid, boric acid, tetrafluoro-potassium phosphate, quaternary ammonium salt, or similar compound.

The coating of the gas-permeable membrane as previously, e.g., Nafion®, may be applied onto the sensor by any suitable means. For example, a solution of the membrane material, e.g., Nafion®, may be used to coat the electrode, and the electrode then may be allowed to dry so as to produce a uniform film. The sensitivity of the gas-permeable membrane-coated electrode sensor is further increased by soaking the electrode sensor in a sodium hydroxide solution for at least about 24 hours and preferably a few days.

The present invention also provides a method of detecting and/or measuring NO concentration in a sample by utilizing the present inventive electrode sensor. NO will directly interact with or bind the polymeric coating on the substrate, thereby changing the redox potential of NO and the electrode sensor so as to change the current drawn through the electrode sensor when employed as a working electrode at a particular potential in a manner related to the concentration of NO in the sample being evaluated. For example, metalloporphyrins, which contain metals such as iron, manganese, nickel, and cobalt, are capable of binding NO and are believed to form metal nitrosyls which provide a different oxidation or reduction potential than NO or the electrode sensor alone. The NO concentration in a sample may be determined by comparing the observed current drawn through the electrode sensor as a working electrode at a fixed potential with the currents observed at the same potential using samples of known NO concentration.

In measuring NO, a two or preferably three electrode system can be employed. The working electrode, comprising the coated carbon fiber, with mesh or plate, is connected to a conductive lead wire (e.g. copper) with conductive (e.g. silver) epoxy, with the lead wire connecting to the voltammetric analyzer, potentiostat or coulometric measuring instrument. The auxiliary or counterelectrode generally comprises a chemically inert conductive material such as a nobel metal (e.g. platinum wire), carbon or tin indium oxide which is also connected to the measuring instrument with a lead wire. In a three electrode system, a reference electrode, such as a standard calomel electrode (SCE), is also employed and connected to the measuring instrument with a third conductive lead wire.

The method of detecting the presence or absence of NO in a sample, therefore, comprises connecting the nitric oxide-specific electrode sensor of the present invention to a potentiostat, such as Model 273 of Princeton Applied Research, calibrating the potentiostat and electrode sensor for a sample known to be devoid of NO, and detecting the presence or absence of nitric oxide in an unknown sample by comparing the measured current to the current for the sample known to be devoid of NO. A change in the observed current indicates the presence of NO in the unknown sample.

Similarly, the method of measuring the concentration of NO in a sample comprises connecting the nitric oxide-specific electrode sensor of the present invention to a potentiostat, calibrating the potentiostat and electrode sensor for samples of known NO concentration, and measuring NO concentration in an unknown sample by comparing the measured current to the current for the samples of known NO concentration.

The present inventive method of detecting and/or measuring NO may be carded out on any suitable sample, although it is preferably carried out in an aqueous sample. The sample may be of a biological or chemical medium, and the evaluation may take place either in vitro or in vivo.

The potential applied to the electrode will depend upon the type of polymeric compound used to coat the substrate. It is preferred that the applied potential have a greater absolute value than the peak potential of the oxidation or reduction reaction in a cyclic voltammogram, e.g., a −0.45 V applied potential for a −0.40 V peak potential, or a +0.55 V applied potential for a +0.50 V peak potential, all relative to a reference electrode potential.

The detection and/or measurement of NO in a sample may be alternatively accomplished by contacting the electrode sensor of the present invention with the sample being tested for some determined period of time sufficient to allow interaction of NO with the electrochemically active polymeric coating and then removing the electrode sensor from the sample, connecting the electrode sensor to a potentiostat previously calibrated for known concentrations of NO, and comparing the observed current with the current for the electrode sensor having been exposed to similar samples of known NO concentration for the same period of time.

The present inventive method of measuring NO concentration is useful in, for example, monitoring NO production of inhibition effected by drugs, in the design of drugs for the treatment of diseases related to defects in NO regulation and/or production, as well as a means of detecting and quantifying defects in NO regulation and/or production, which result from disease, injury, and mutation, all in vitro or in vivo.

The present invention additionally provides a means of monitoring pollution of which NO is a component.

In use, then the working electrode, with the other electrode(s) in proximity, is placed into the analytic solution. It will be appreciated that by "analytic solution" is meant any aqueous or nonaqueous solution in which NO is to be detected or measured. The term thus includes both chemical and biological media, including tissue fluids and extracellular and cellular fluids. It will also be appreciated that the sensor of the invention can be used qualitatively to detect the presence of NO and also quantitatively to measure the levels of NO present in the analytic solution. To detect or measure NO release in a single biological cell, a microsensor of appropriate dimension can be either inserted into or placed close to the cell membrane.

The cell membrane surface concentration of NO is influenced by the following factors release of NO due to the action of bradykinin, adsorption and chemisorption of NO on the surface of the cell membrane, oxidation by $O_2$ and organic molecules, and diffusion into other cells and to the bulk solution. The decay in NO response following the addition of standard amounts of oxygen was studied. Decreases of only 22% and 35% were observed after 4 and 10 min. respectively, following the addition of 100 µM $O_2$ to a 20 µM NO solution in the absence of biological material. These measurements in the presence of $O_2$ indicate that its role in the oxidation of NO may have been overestimated, and that NO oxidation is due mainly to the biological material as was previously suggested by Monocada. See Moncada, S. et al., *Pharmacol. Rev.* 43:109–142 (1991).

The following examples serve to further illustrate the present invention and are not intended to limit the scope of the invention.

Preparation—Example 1

This example illustrates the preparation of several TMPP-coated NO electrode sensors.

A glassy carbon electrode (GCE, diameter=2 mm) was coated with the conductive polymeric porphyrin $Ni^{2+}$ tetramethylpyridylporphyrin (TMPP, prepared for use in this example although commercially available from Midcentury Chemicals, Posen, Ill.) (see FIG. 1c) by cyclic voltammetry employing a platinum rod as an auxiliary electrode and a standard calomel electrode (SCE) as a reference electrode in a 5 ml solution of 0.1M NaOH and the monomeric porphyrin and cycling between 0 and +1.0 V (versus SCE) for 15 cycles at a 50 mV/sec scan rate. Glassy carbon electrodes were similarly prepared using $Co^{2+}$ and $Fe^{3+}$ TMPP, except using a controlled potential, rather than the cyclic voltammetry, of about +0.75 V (versus SCE) maintained for about 4 minutes.

Preparation Example 2

This example illustrates the treatment of a $Ni^{2+}$ TMPP-coated NO electrode sensor to render it insensitive to interference from nitrite during measurements of NO concentration in samples.

Possible sources of interference in measuring NO with the electrode sensor include nitrite, nitrate, and nitrous oxide. Nitrate ions and nitrous oxide do not generate a response in the examined potential range, i.e., +0.4 V to +0.9 V. A response to nitrite can be obtained in the examined potential range, although the response to NO is 100 times more sensitive than the response to nitrite.

In order to eliminate the interference from nitrite and other ions, the $Ni^{2+}$ TMPP-coated NO electrode sensor of Example 1 was further coated with Nafion®. The Nafion® coating was effected by exposing the electrode sensors to 4 µl of a commercially available Nafion® solution comprising 5 wt. % Nafion® in a mixture of lower aliphatic alcohols and water (9:1) (Aldrich Chemical Co.) and then allowing the Nafion® coating to dry so as to generate a uniform film on the electrode sensor. This Nafion® electrode sensor was then soaked in a 0.01M NaOH solution for 24 hours.

Preparation Example 3

This example illustrates the preparation of a DME-coated NO electrode sensor.

Protoporphyrin IX dimethyl ester (DME, Porphyrin Products, Logan, Utah) was metalated with iron in dimethyl formamide at 100° C. by a standard procedure (Mikami et al., J. Biochem. (Tokyo) 105: 47. 1989.). A glassy carbon electrode (diameter=2 mm) was coated with the conductive polymeric porphyrin iron (III) protoporphyrin IX dimethyl ester (see FIG. 1d) by immersing the electrode in an argon-blanketed dichloromethane solution (1.0 mM) of the metalloporphyrin monomer and cycling the electrode potential repeatedly between 0.0 and +1.3 V vs. SCE. After electropolymerization, the coated electrode was rinsed thoroughly with pure solvent.

SPECIFIC EXAMPLE I

This example illustrates the use of TMPP-coated electrode sensors to measure NO concentration in aqueous solutions.

A carbon macroelectrode covered with conductive porphyrin polymer was prepared as follows. A glassy carbon electrode (GCE) (diameter about 2 mm) was coated with conductive polymeric porphyrins by cyclic voltammetry or controlled potential oxidation (4 min) at 0.7 V vs SCE of the monomeric porphyrin in 0.1M NaOH solution (5 ml). The auxiliary electrode was a platinum (Pt) rod and the reference electrode was a standard calomel electrode (SCE). The porphyrin-coated (about 0.8–1.5 $nm/cm^2$) electrode was removed from the solution and stored in 0.1M base. The porphyrins used were $Ni^{2+}$, $Co^{2+}$, or $Fe^{3+}$ TMHPP or PUP as shown in FIGS. 1a, b, c and d. The porphyrin-coated electrodes were then further coated with 4 µl of 5% Nafion® solution.

A stock solution of saturated nitric oxide was prepared anaerobically in pH=7.4 (0.1M) phosphate buffer. This stock solution was then added in the correct volume to obtain the desired final concentration of NO (10, 20 and 40 µM). The electrochemical cell had a Pt rod counter electrode and SCE reference electrode and the working electrode was the glassy carbon electrode coated with polymeric porphyrin film and Nafion®, as described above. It will, also be appreciated that a two electrode arrangement, i.e. the working and auxiliary electrode, can be utilized. Measurements were performed in 5 ml phosphate buffer (pH=7.4, 0.1M) which served as the supporting electrolyte. All solutions were degassed prior to use and kept under nitrogen. A base line scan was taken using linear sweep voltammetry (range=0 to +0.9 V vs SCE) or differential pulse voltammetry (range=+0.4 to 0.9 V vs SCE). Aliquots of the NO stock solution were introduced to the cell via a gas-tight syringe. The final dilution of the NO stock solution in the phosphate buffer was taken as the final NO concentration.

Figure 2:
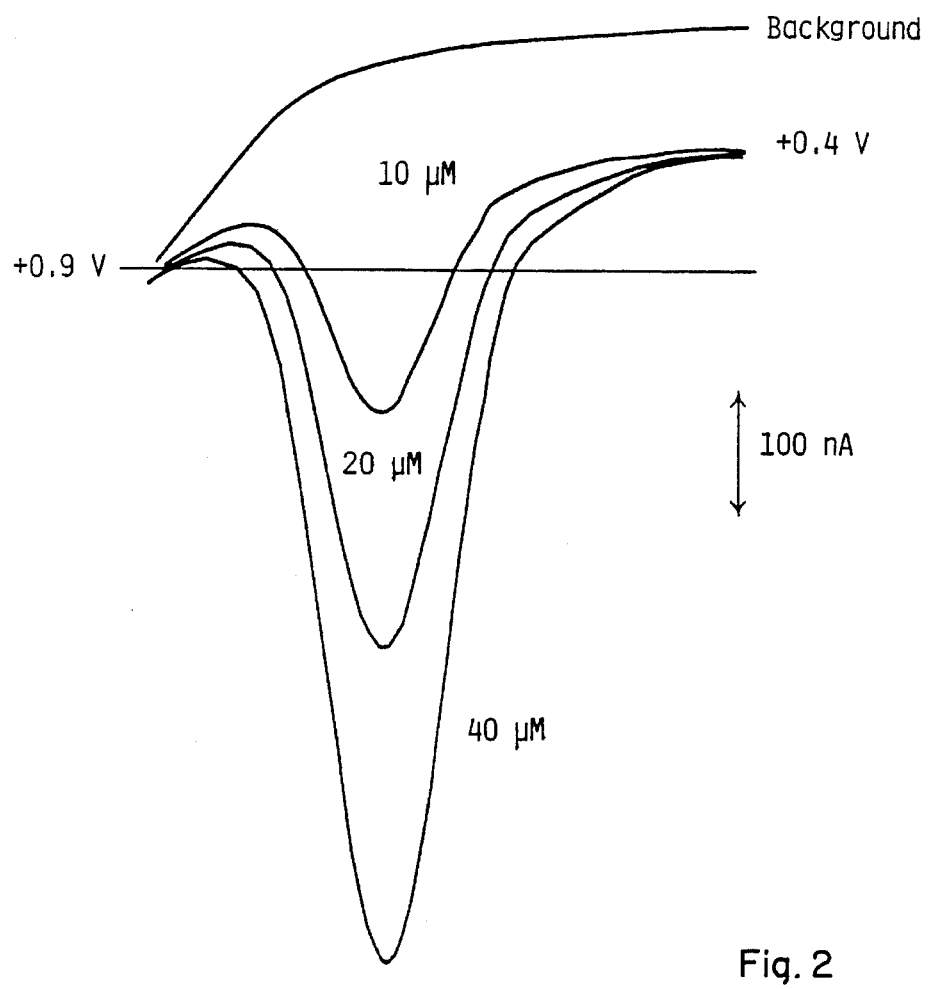
FIG. 2 is a differential pulse voltammogram of NO at various concentrations. More specifically.
Figure 3:
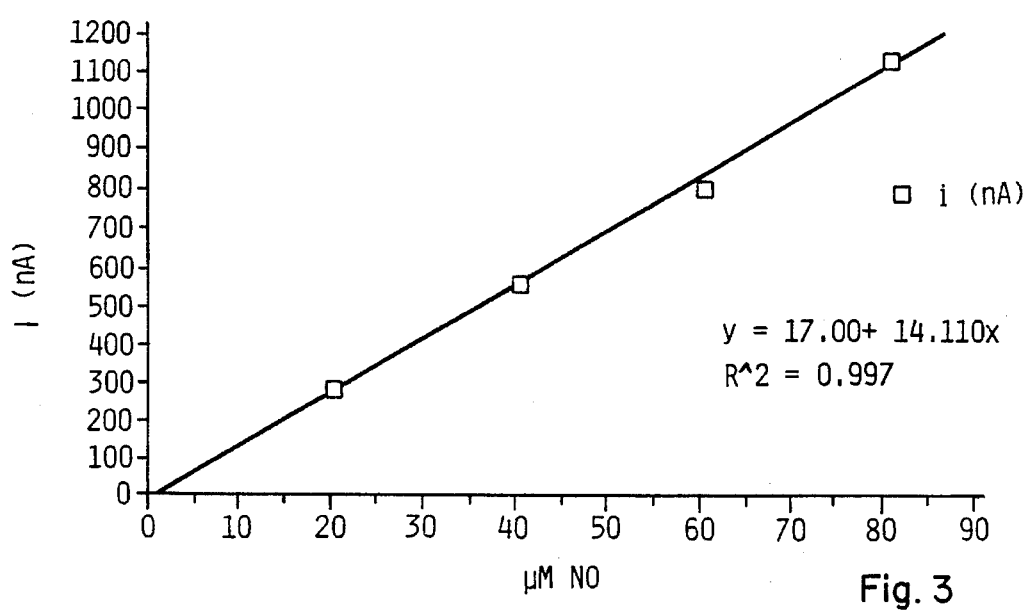
FIG. 3 is a graph showing nitric oxide response (nA) of NO solutions measured by a sensor of the invention. More specifically.
Figure 5:
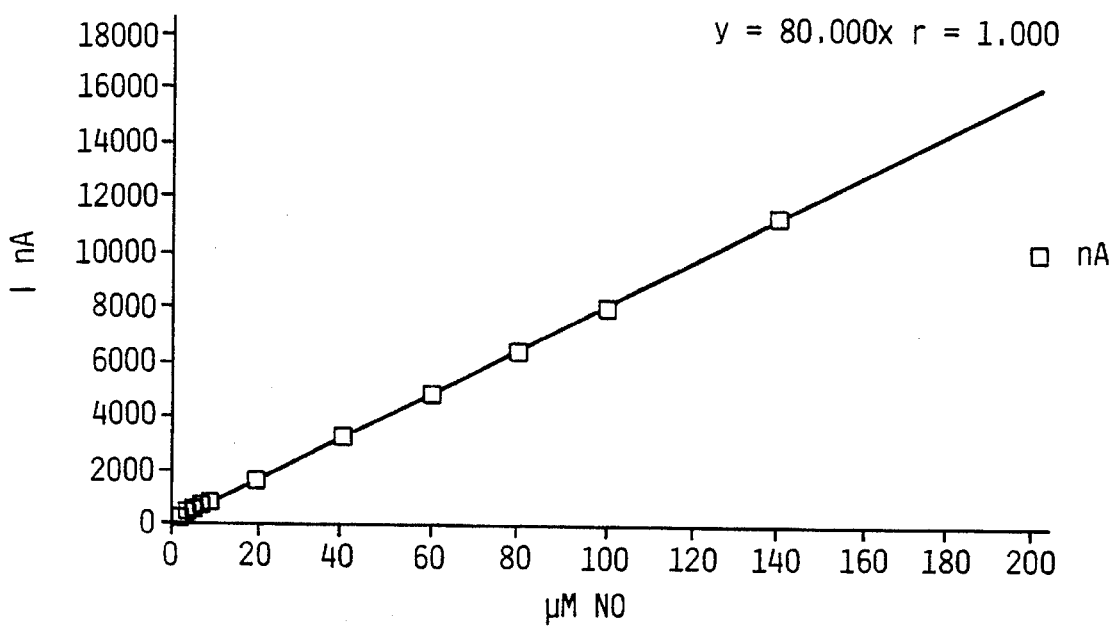
FIG. 5 is a graph of current (i, nA) versus NO concentration (μM) prepared using a GCE/Fe(III) TMPP electrode with 4 μl Nafion®, which shows the NO response of NO solutions of varying NO concentration in 0.1M phosphate buffer, pH=7.4, prepared from a saturated solution of NO at room temperature.

The response obtained by differential pulse voltammetry using the $Ni^{2+}$ TMPP electrode of Preparation Example 2 with 10, 20, and 40 µM NO solutions is shown in FIG. 2 (anodic peak (oxidation) potential (EPA)=0.7 V vs. SCE). A linear response of current versus NO concentration was observed for the same electrode for concentrations of NO of 20, 40, 60, and 80 µM as shown in FIG. 3 (Epa=0.7 V vs. SCE). A linear response of current versus NO concentration was similarly observed for the $Fe^{3+}$ TMPP electrode of Preparation Example 1 for concentrations of NO up to 140 µM as shown in FIG. 5 (Epa=0.7 V vs. SCE).

Figure 4:
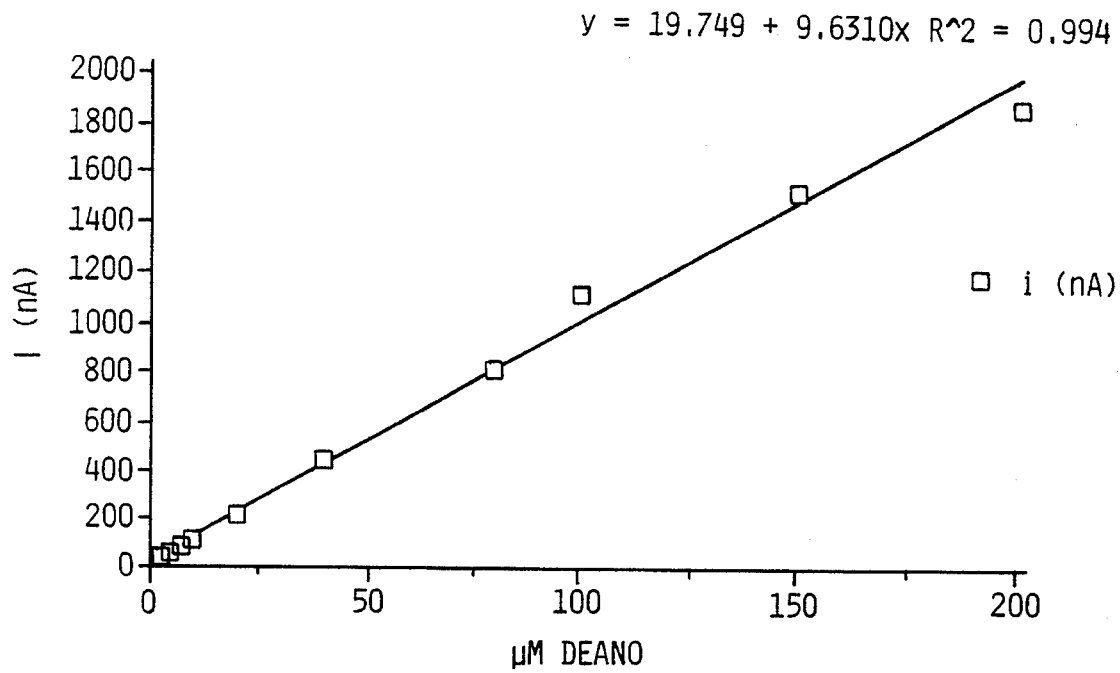
FIG. 4 is a graph of current (i, nA) versus DEANO concentration (μM) prepared using a GCE/Ni (II) TMPP electrode coated with 4 μl Nafion®, which shows the NO response of DEANO solutions of varying DEANO concentration in 0.1M phosphate buffer, pH=7.4, prepared from a 11.2 mM solution of DEANO in 0.01M NaOH at room temperature.

Measurements were also taken for the NO-releasing compound {$Et_2N$-N(N=0)–0}Na, known as DEANO (Maragos et al., J. Med. Chem. 34: 3242–3247. 1991.), and a linear response of current versus DEANO concentration was observed for the $Ni^{2+}$ TMPP electrode of Preparation Example 2 for DEANO concentrations up to 200 µM as shown in FIG. 4 (Epa =0.7 V vs. SCE).

SPECIFIC EXAMPLE II

This example illustrates the use of a DME-coated electrode sensor to measure NO concentration in aqueous solutions.

A stock solution of saturated NO was prepared anaerobically in 0.1M phosphate buffer at pH 7.4. The stock solution was then used to prepare aqueous solutions of NO at desired concentrations. All solutions were freshly degassed and stored under nitrogen prior to use.

An electrochemical cell was prepared with a platinum rod counter electrode, a SCE reference electrode, and the DME-coated glassy carbon working electrode prepared in accordance with Example 3. A 0.1M phosphate buffer at pH 7.4 was used as the supporting electrolyte during measurement of NO concentration. All measurements were performed in 5 ml of the phosphate buffer.

A baseline scan was taken using differential pulse voltammetry (range=+0.4−+0.9 V vs. SCE). Linear sweep voltammetry (range=0−+0.9 V vs. SCE) could have been similarly used to determine a baseline.

Aliquots of the NO stock solution were introduced into the electrochemical cell by means of a gas-tight syringe. The final dilution of the NO stock solution in the phosphate buffer was taken as the final NO concentration.

Figure 6A:
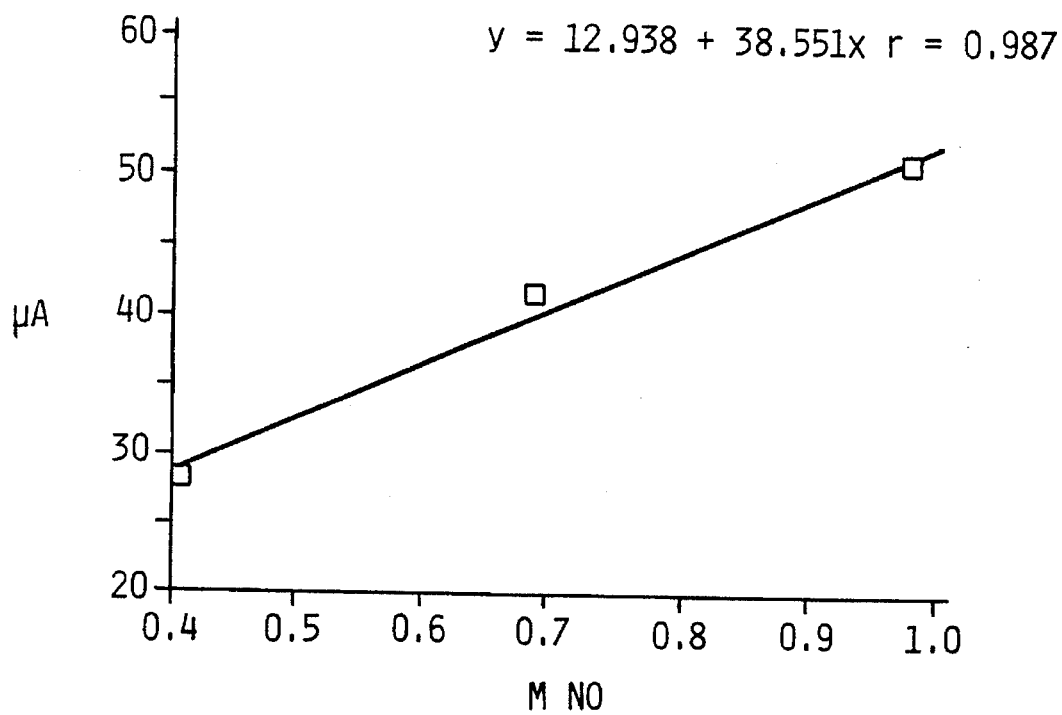
FIGS. 6a and 6b are graphs of current (i, μA) versus NO concentration (M) prepared using a 0.0707 $cm^2$ GCE/Fe(III) DME electrode and linear sweep voltammetry (scan rate=20 mV/s), which shows the NO response of NO solutions of varying NO concentration in 0.1M phosphate buffer, pH=7.4, prepared from a saturated solution of NO at room temperature.
Figure 6B:
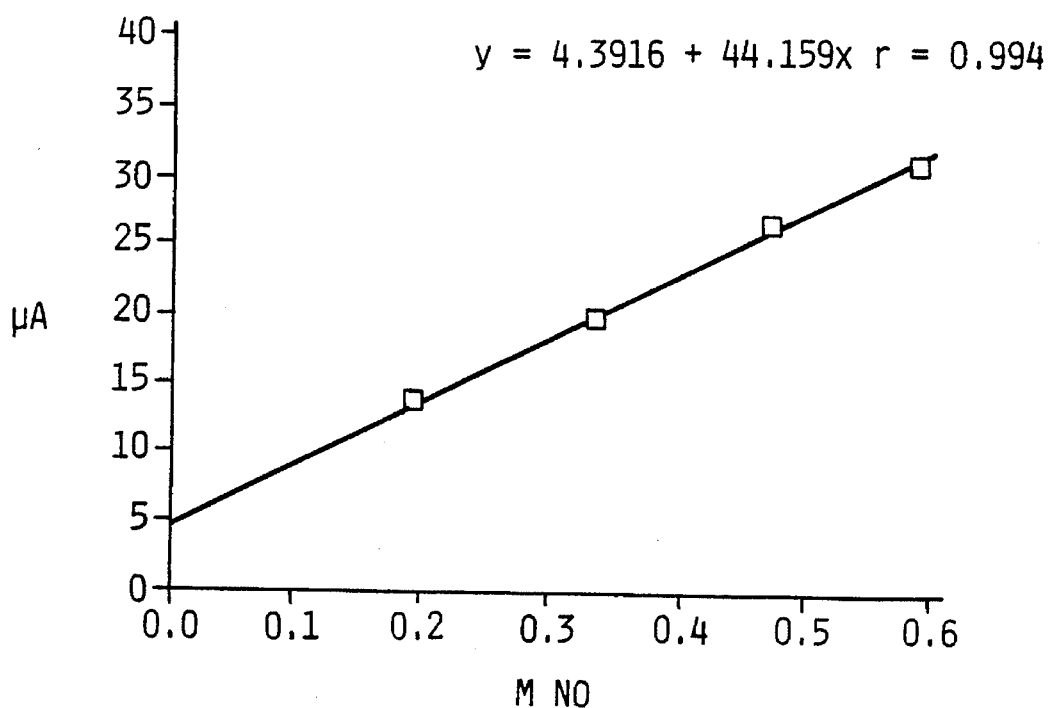

A linear response of current versus NO concentration was observed for the $Fe^{3+}$ DME electrode of Example 3 for concentrations of NO of 0.2 to 1.0M NO as shown in FIGS. 6a and 6b. (Epa=0.7 V vs. SCE).

SPECIFIC EXAMPLE III

This example further illustrates the use of an $FE^{3+}$ DME-coated NO electrode sensor to measure NO concentration in an aqueous solution.

A stock solution of saturated NO was prepared anaerobically in 0.1M phosphate buffer at pH 7.2. The stock solution was then used to prepare aqueous solutions of NO at desired concentrations. All solutions were freshly degassed and stored under nitrogen prior to use.

An electrochemical cell was prepared with a platinum rod counter electrode, a SCE reference electrode, and a Fe(III) DME-coated glassy carbon working electrode, prepared in accordance with Example 3. A 0.1M phosphate buffer at pH 7.2 was used as the supporting electrolyte during measurement of NO concentration. All measurements were performed in 5 ml of the phosphate buffer.

A baseline scan was taken using cyclic voltammetry (20 mV/sec, cathodic peak (reduction) potential (Epa)=−1.0 V vs. SCE). Differential pulse voltammetry could have similarly been used to establish a baseline.

Aliquots of the NO stock solution were introduced into the electrochemical cell by means of a gas-tight syringe. The final dilution of the NO stock solution in the phosphate buffer was taken as the final NO concentration.

Figure 7:
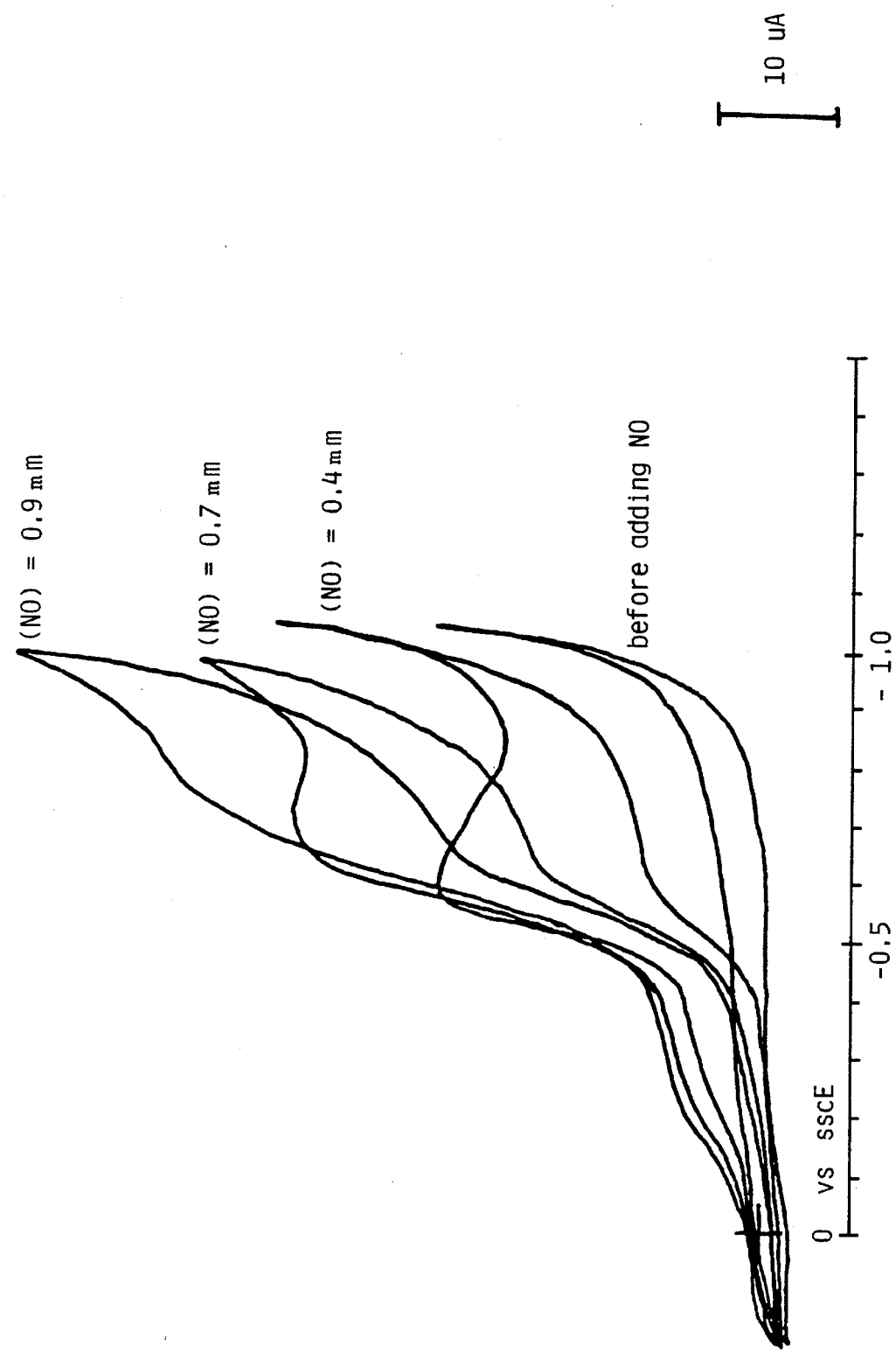
FIG. 7 is a graph of current versus (i, μA) versus potential (V) prepared using a GCE/Fe(III) DME electrode and cyclic voltammetry (scan rate=20 mV/sec), which shows the current response of NO solutions of varying NO concentration in 0.1M phosphate buffer, pH 7.2, at room temperature.
Figure 8A:
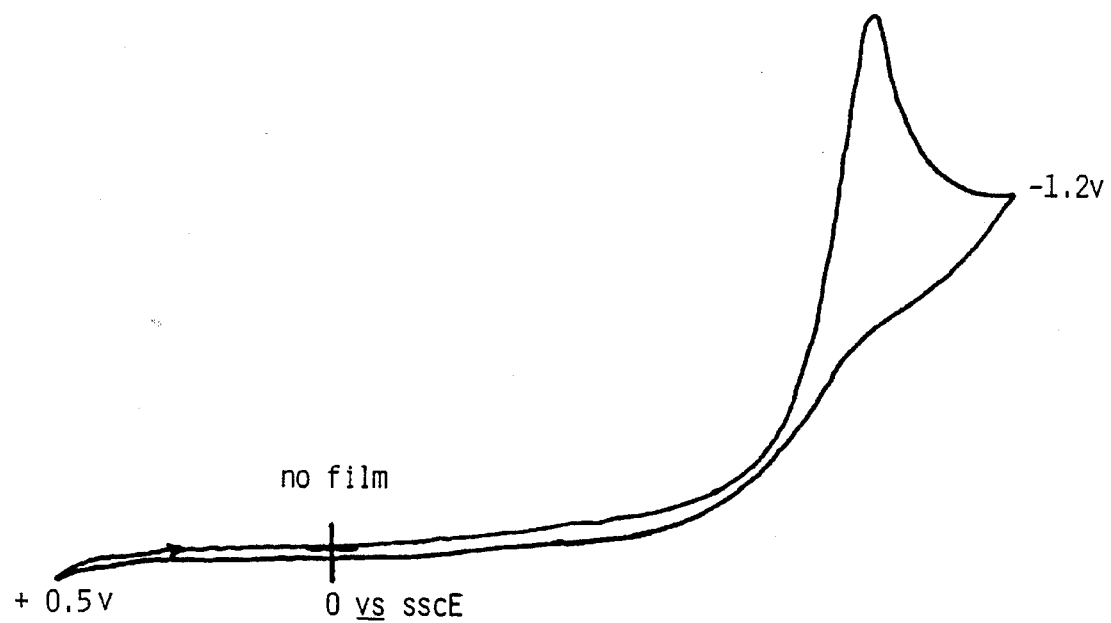
FIGS. 8a and 8b are graphs of current (i, μA) versus potential (V) prepared using a GCE electrode and a GCE/Fe(III) DME electrode, respectively, and cyclic voltammetry (scan rate=20 mV/sec), which shows the current response of 2 mM NO solution in 0.1M phosphate buffer, pH 7.2, at room temperature.
Figure 8B:
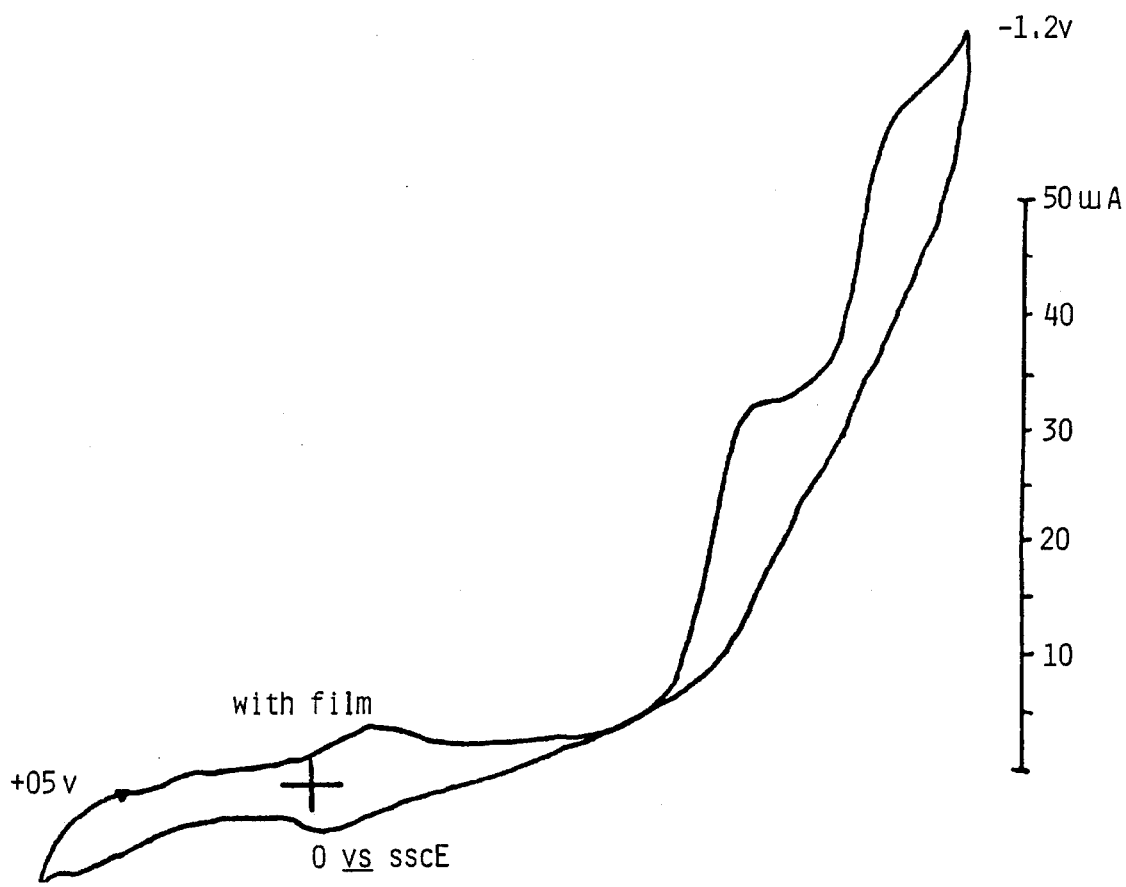

The response obtained by cyclic voltammetry using the $Fe^{3+}$ DME electrode of Example 3 with 0, 0.4, 0.7, and 0.9 µM NO solutions is shown in FIG. 7 (cathodic peak (reduction) potential (Epa)=−1.0 V vs. SCE). The responses obtained by cyclic voltammetry using the a GCE electrode without any electrochemically active polymeric coating and the $Fe^{3+}$ DME electrode of Preparation Example 3 with 2 mM NO solutions were then compared as shown in FIG. 8a and 8b, respectively. In contrast to the $Fe^{3+}$ DME electrode sensor, the glassy carbon electrode without the electrochemically active polymeric coating was relatively unresponsive to NO concentration.

SPECIFIC EXAMPLE IV

Carbon microfiber conductive supports for the microsensor were produced by threading an individual carbon fiber (7 µm) through the pulled end of a capillary tube with approximately 1 cm left protruding. Non-conductive epoxy was put at the glass/fiber interface. When the epoxy that was drawn into the tip of the capillary dried, the carbon fiber was sealed in place. The carbon fiber was sharpened following standard procedure using a microburner. See Bailey, F. et al., *Anal. Chem.* 63:395–398 (1991). The sharpened fiber was immersed in melted wax-resin (5:1) at controlled temperature for 5–15 sec. After cooling to room temperature, the fiber was sharpened again. During burning, the flame temperature and the distance of the fiber from the center of the flame need to be carefully controlled. While the diameter of the sharpened lip is smaller, the tip length is larger, with the overall effect of the resulting electrode being a slim cylinder with a small diameter rather than a short taper. This geometry aids in implantation and increases the active surface area. Scanning electron microscopy of the fiber produced shows that the wax is burned approximately to the top of the sharpened tip. The area of the tip, controllably fabricated with appropriate dimensions, is the only part of the carbon fiber where electrochemical processes can occur. A typical length of the electrochemically active tip is between 4–6 µm. For the sensor to be implanted into a cell, this length must be smaller than the thickness of the cell. The unsharpened end of the carbon fiber was attached to a copper wire lead with silver epoxy.

Figure 9A:
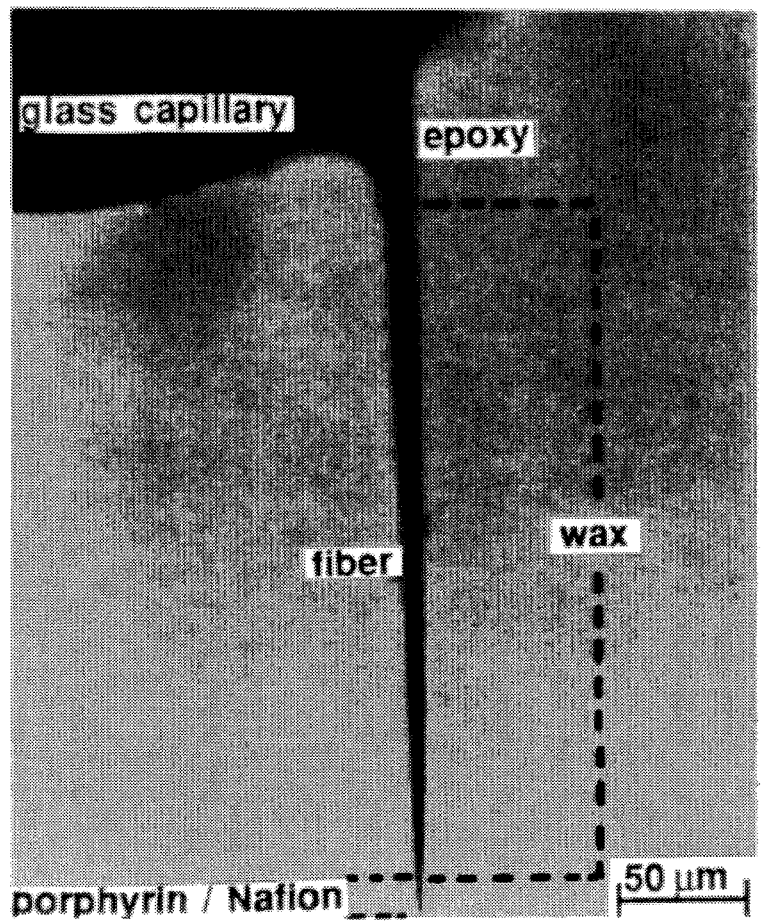
FIG. 9a is a microscopic photograph of a carbon fiber microsensor of the present invention.
Figure 9B:
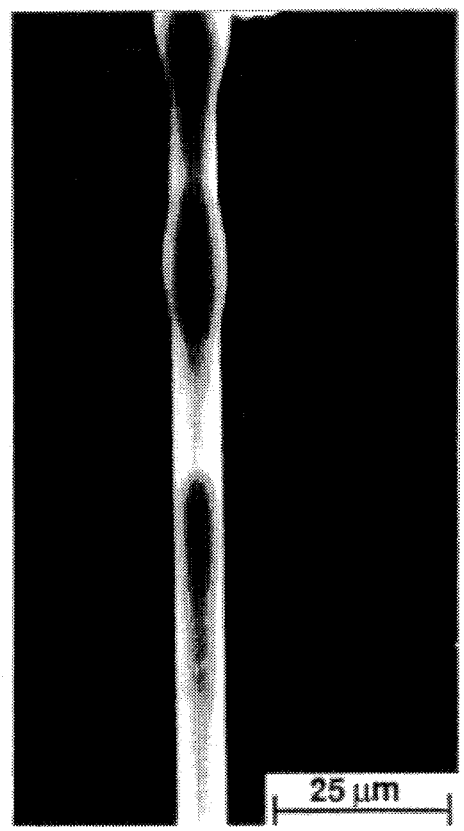
FIG. 9b is an electron scanning micrograph of the portion of the microsensor covered with a coat of isolating wax-resin mixture.
Figure 9C:
FIG. 9c is an electron scanning micrograph of the thermally-sharpened tip of the microsensor covered with conductive polymeric porphyrin.

Referring now to the Figures, FIG. 9a is a microscopic photograph of a completed NO microsensor of the present invention. FIG. 9b is an electron scanning micrograph illustrating the part of the microsensor covered with the coat of isolating wax-resin mixture. FIG. 9c is an electron scanning micrograph of the thermally-sharpened tip of the microsensor covered with conductive polymeric porphyrin and Nafion® as described below.

SPECIFIC EXAMPLE V

Figure 10:
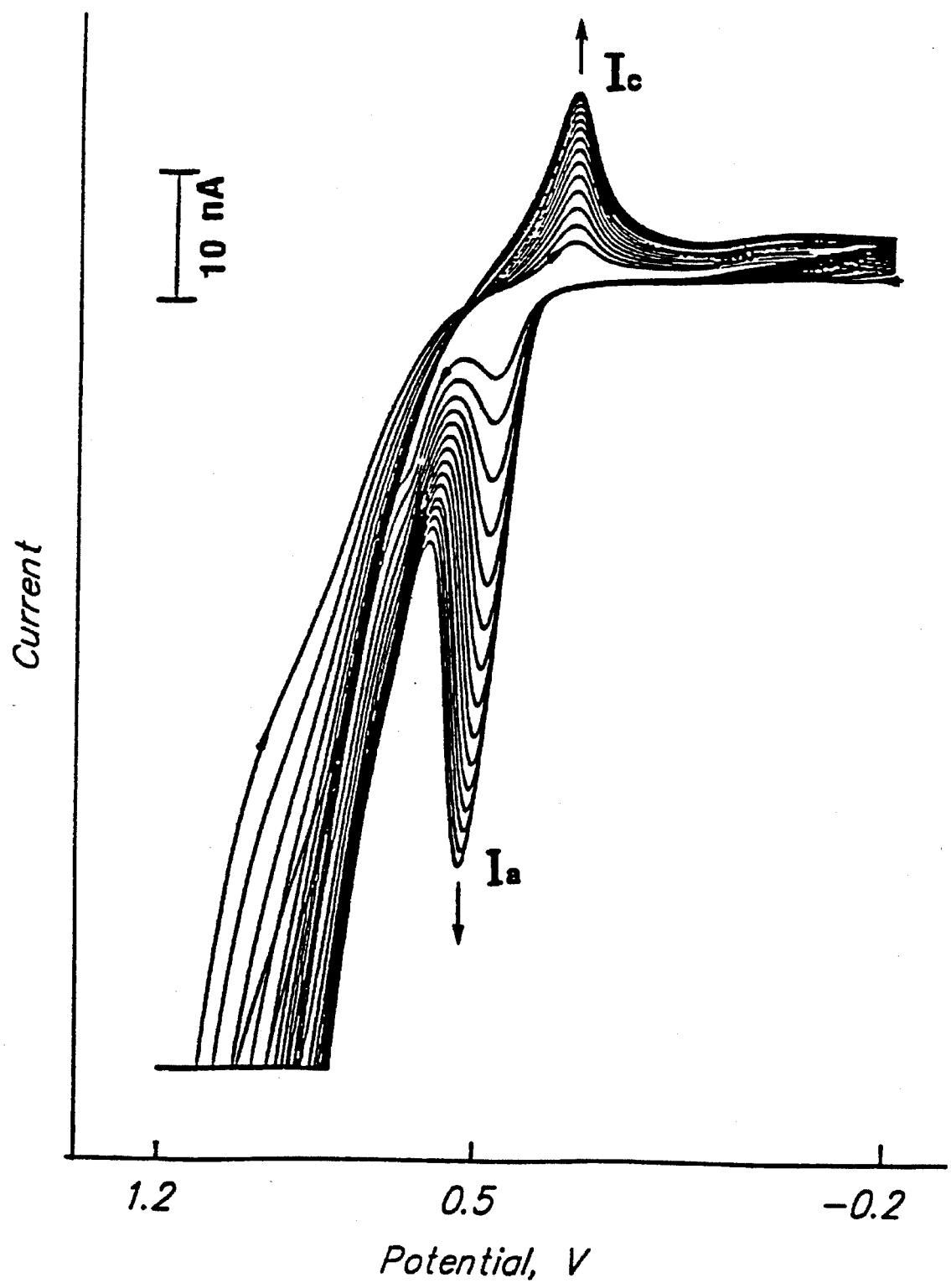
FIG. 10 is a scan showing the growth patterns for poly-TMHPPNi, deposited from $5 \times 10^{-4}$M TMHPPNi, 0.1M NaOH solution by continuous scan cyclic voltammetry on a carbon fiber microelectrode.

The growth patterns for poly-TMHPPNi were examined. Poly-TMHPPNi was deposited from a solution of 0.1M NaOH containing $5 \times 10^{-4}$M monomeric tetrakis(3-methoxy-4-hydroxyphenyl)porphyrin (TMHPP), with Ni as a central metal (TMHPPNi) by continuous scan cyclic voltammetry from 0.0 to 1.1 V, on a carbon fiber microelectrode (16 µm² surface area), as generally described in [16]. As shown in FIG. 10, peaks 1a and 1c correspond to the oxidation of Ni(II) to Ni(III) and reduction of Ni(III) to Ni(II), respectively, in the film. The Ni(II)/Ni(III) redox couple observed at 0.5 V allows porphyrin surface coverage, (Γ), to be monitored (optimal Γ=0.7–1.2 nmol cm²). Surface coverage is calculated from the charge transferred under process 1a (Γ=0.8 nM/cm²). The surface coverage depends upon the initial concentration of TMHPPNi, electrolysis time and potential.

Following deposit on the fiber, the porphyrin film was conditioned by 5–10 scans from 0.4 to 0.9 V. At this stage, the electrode should be stored in 0.1M NaOH. Sensor fabrication was completed by dipping in the Nafion® solution (5%) for 15–20 sec and left to dry (5 min) and stored in pH 7.4 buffer. Since the Ni(II)/Ni(III) reaction requires diffusion of OH⁻ to neutralize a charge generated in the poly-TMHPPNi and OH⁻ cannot diffuse through Nafion®, the later absence of the Ni(II)/Ni(III) voltammetric peaks in 0.1M NaOH demonstrated the integrity of the Nafion® film coverage.

SPECIFIC EXAMPLE VI

NO monitoring was done by differential pulse voltammetry using a classic three electrode system; the sensor as the working electrode, a saturated calomel electrode (SCE) reference electrode and a platinum (PE) wire auxiliary electrode. The pulse amplitude was 40 mV and the phosphate buffer solution was pH 7.4. Differential pulse voltammograms were obtained for oxidation of NO on poly-TMHPPNi without Nafion® (depicted as A in FIG. 11) and with Nafion® (depicted as C in FIG. 11) and for 1 µM NO in the presence of 20 µM $NO_2^-$ on poly-TMHPNi without Nafion® (depicted as B in FIG. 11) and with Nafion® (depicted as D in FIG. 11).

Figure 11A:
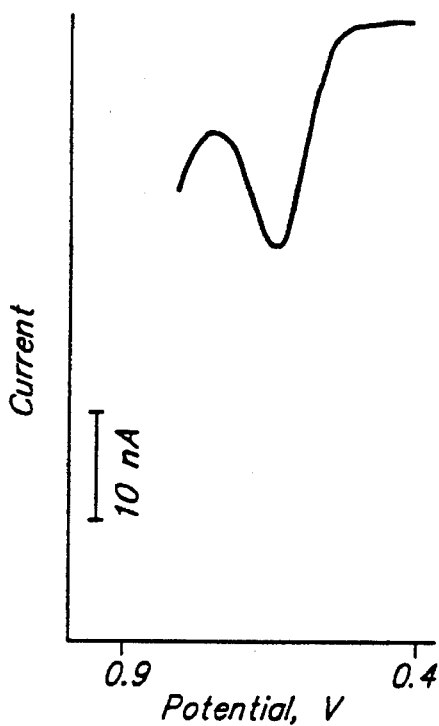
FIGS. 11a, b, c and d are voltammograms showing the response of the microsensor in the differential pulse voltametric mode.
Figure 11B:
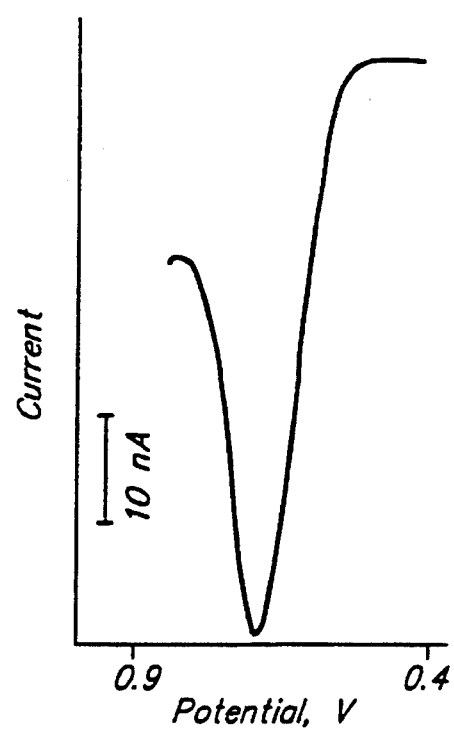
Figure 11C:
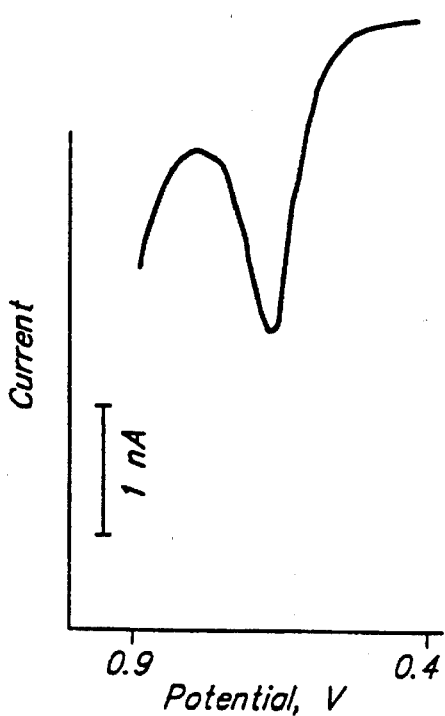
Figure 11D:
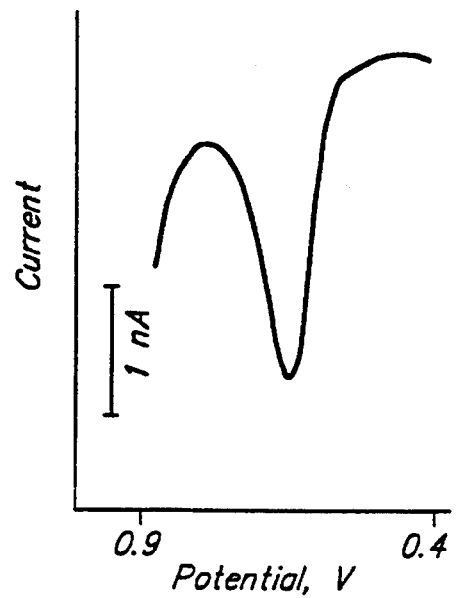

DPV of NO on poly-TMHPPNi without Nafion showed a peak at 0.63 V in buffer pH 7.4 (see FIG. 11a). DPV of a solution of 1 μM NO and 20 μM $NO_2^-$ showed a single peak at 0.80 V (see FIG. 11b). The peak current was thus three times higher than that observed at 0.63 V for NO alone. This indicated that the oxidation of $NO_2^-$ and NO occur at a similar potential, but that the current increase is not proportional to the concentration of $NO_2^-$. The NO peak current with the Nafion®-coated sensor was observed at 0.64 V (see FIG. 11c). Although the observed current is lower, Nafion® coverage provides high selectivity against $NO_2^-$. Only a 1% increase in current and no change of potential was observed for oxidation of 1 μM NO in the presence of 20 μM $NO_2^-$ (see FIG. 11d). Thus the porphyrinic microsensor was selective for NO and insensitive for $NO_2^-$ up to a ratio of at least 1:20.

A linear relationship was observed between current and NO concentration up to 300 μM (r=0.994:slope=205 nA/μM;n=21). The response time (time for the signal increase from 10% to 75%) in the amperometric mode was less that 10 milliseconds. The detection limit calculated at a signal/noise ration=3 was 20 nM for DPV and 10 nM for the amperometric method. Since, in a volume equivalent to that of an average single cell ($10^{-12}$ L), about $10^{-2}$ attomoles ($10^{-2}$ moles) of NO can be detected, the detection limit of the sensor is 2–4 orders of magnitude lower than the estimated amount of NO released per single cell (1–200 attomol/cell)[12,13].

SPECIFIC EXAMPLE VII

Amperometric detection of NO by the microsensor under various biological conditions was also studied. Ring segments from porcine aorta (about 2–3 mm wide) and porcine aorta endothelial cell culture were prepared according to previously described procedures.[17] Using a computer controlled micropositioner (0.2 mm X-Y-Z resolution), the microsensor could be implanted into a single cell, or placed on the surface of the cell membrane, or kept at a controlled distance from the cell membrane.

Figure 12A:
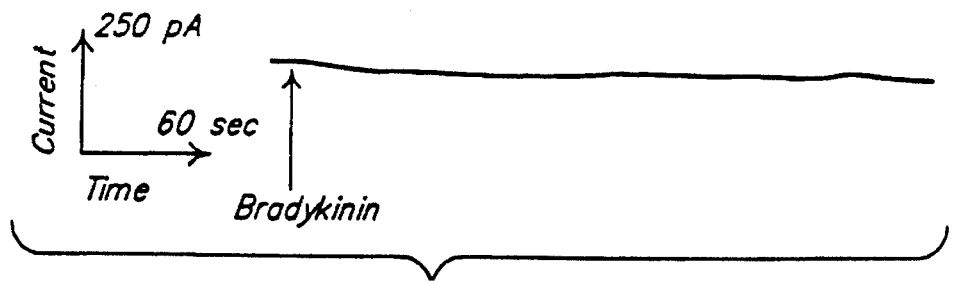
FIG. 12a, b, c and d are scans showing the response of the microsensor in the amperometric mode.
Figure 12B:
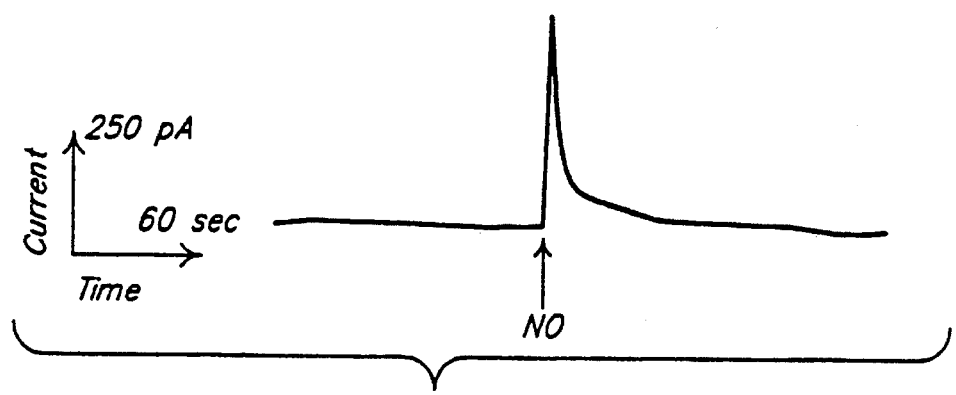
Figure 12C:
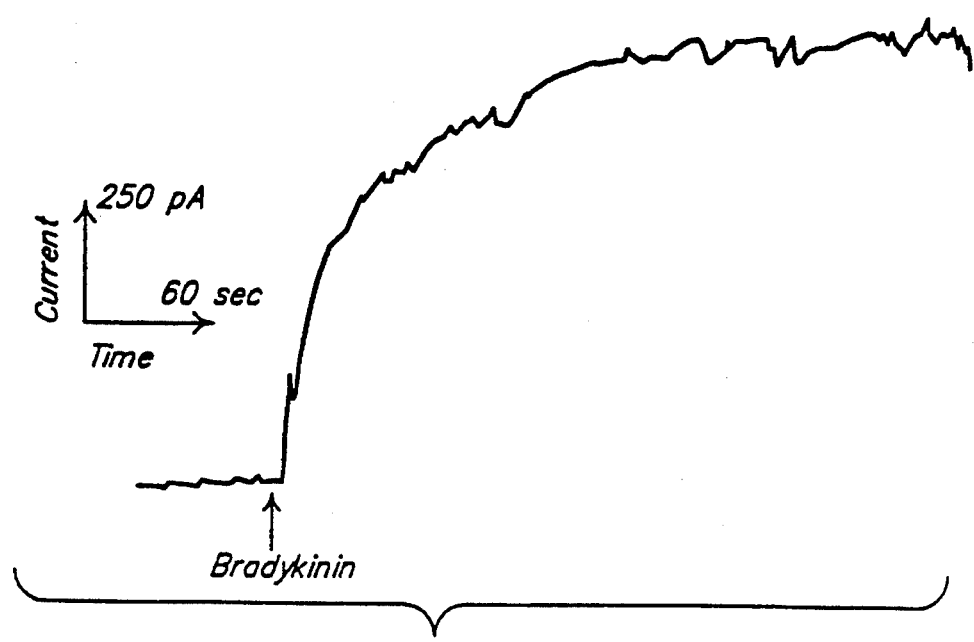
Figure 12D:
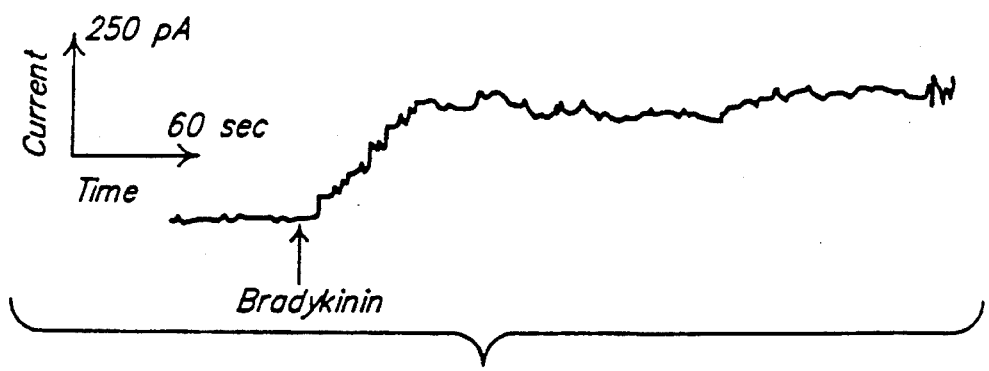

Alternating current was measured in three electrode systems, as described above, at constant potential of 0.75 V modulated with 40 mV pulse in time intervals of 0.5 sec. The background, shown in FIG. 12a, was measured in cell culture medium at 37° C. (DMEM-Dulbecco's Modified Eagle Medium, 100 mg/L D-glucose, 2 mM glutamine, 110 mg/L sodium pyruvate, 15% controlled process serum replacement TYPE 1). No change of the background was observed after the addition of 50 nM of bradykinin to 5 ml of cell culture medium. As shown in FIG. 12b, 2 nm of NO were injected by microsyringe into the cell culture medium, a 5 mm distance from the microsensor. As shown in FIG. 12c, one microsensor was placed on the surface of the single endothelial cell in the aortic ring, and another was implanted into the smooth muscle cell. 2 nm of bradykinin was injected into the medium near the endothelial cell. After 3±0.5 sec (n=7), NO release was detected and a steady increase of surface concentration to a plateau at 450±40 nM was observed after 200 sec (see FIG. 12c). After 16 min, the surface concentration of NO decreased to zero. No significant difference in NO surface concentration was found for the endothelial cell from cell culture (430±40 nM, n=7). NO was detected in a single smooth muscle cell within 6.0±0.5 sec (n=7) after injection of bradykinin and a maximum concentration (130±10 nM, n=7) was observed after 90 sec (see FIG. 12d). The observed current indicates that the initial concentration around the sensor is 230 nM and decreases to 40 nM after 17 sec due mainly to depletion of NO by diffusion and also reaction with $O_2$.

SPECIFIC EXAMPLE VII

Figure 13A:
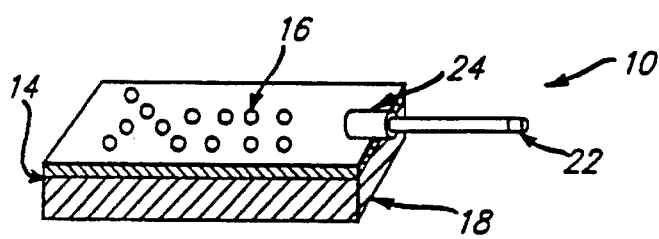
FIG. 13a–c are schematic overviews of macrosensors of the present invention used in cell culture.
Figure 13B:
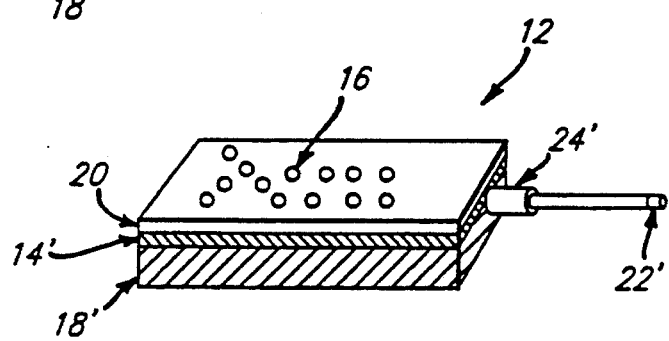

Sensors utilizing a layer of tin indium oxide on a glass plate base used as either a counterelectrode or as the conductive layer of a working electrode were also constructed. FIG. 13a illustrates the use of a layer of indium oxide (14) as a counterelectrode (10), (10), whereas FIG. 13b illustrates its use as a conductive layer of the working electrode of a macrosensor (12). BCH1 myocytes (16) were grown under standard culture conditions at $2\times10^7$ cell/cm$^2$ on a glass plate (18) (FIGS. 13a and c) or on a plate layered with catalytic polymeric iron porphyrin with Nafion® coated thereon (20) (FIG. 13b). As shown in FIGS. 13a and b the tin indium oxide semiconductor layer in both cases was attached to the measuring instrument by a copper wire lead (22) with silver epoxy (24).

Figure 14:
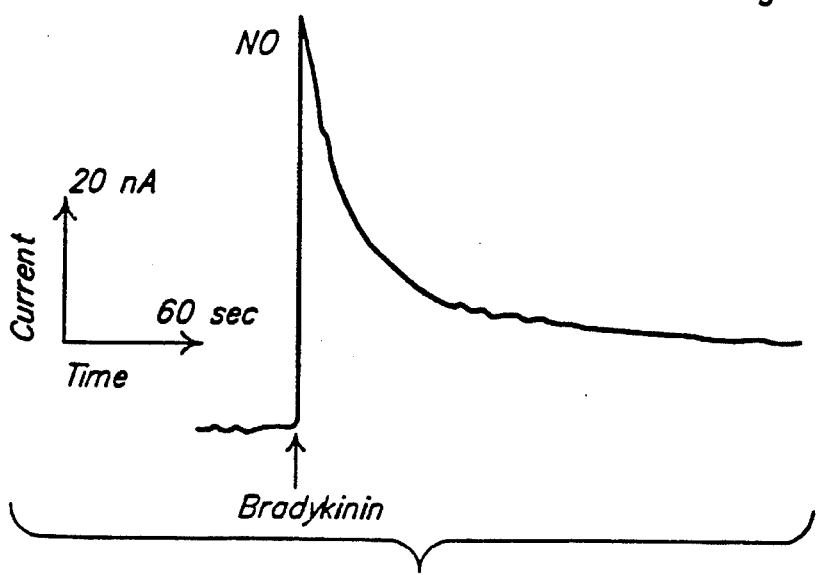
FIG. 14 shows the response of a platinum mesh macrosensor to NO release by a cell culture grown directly on the sensor surface.
Figure 13C:
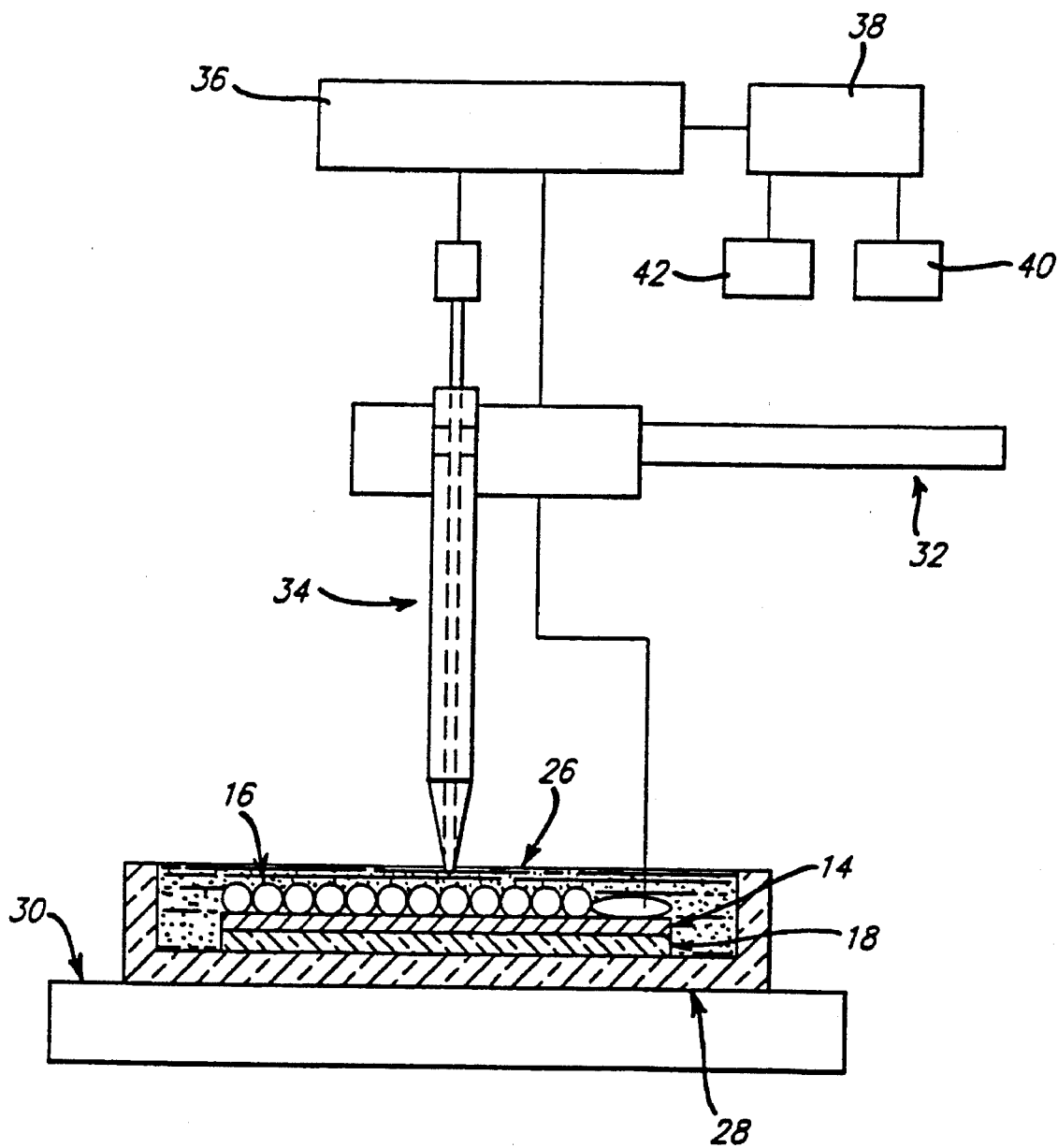

The schematic of FIG. 13c depicts the set up for NO measurements of the cell culture in FIG. 13a. Cells were grown on a tin indium oxide (14) layered glass plate (18) placed in a Petri dish (20) with standard culture media (26). A microsensor working electrode (34) constructed as described in previous Examples was then used to measure NO release in situ. The culture was microscopically monitored (30⁻ inverted microscope) and the working electrode positioned with a micromanipulator (32). As shown in FIG. 13c, microsensor was attached to a measuring instrument such as a voltammetric analyzer (36) with the results fed to a computer (38) connected to a plotter (40) and printer (42) for result readout. NO response results observed were on the order of those in the previously described Specific Examples. Similar results were also obtained in cell cultures grown on fine platinum mesh and are shown in FIG. 14.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as described herein and defined in the following claims. It is intended that the invention may be practiced otherwise than as specifically described herein. Accordingly, this invention includes all modifications encompassed within the spirit and scope of the invention as defined by the following claims.

All publications cited herein are incorporated by reference.

What is claimed is:

1. A nitric oxide-specific electrode sensor, which comprises:
   an electrically conductive substrate whose amperometric response is substantially unaffected by the presence of nitric oxide; and
   an adherent and substantially uniform electrochemically active polymeric coating formed on a surface of said electrically conductive substrate which interacts with NO to change the redox potential of NO and the electrode sensor.

2. The electrode sensor of claim 1, wherein said electrochemically active polymeric coating is formed on the surface of said electrically conductive substrate by electrolytic polymerization.

3. The electrode sensor of claim 2, which additionally comprises a gas-permeable membrane coating that is permeable to nitric oxide and is not permeable to nitrite.

4. The electrode sensor of claim 1, wherein said electrically conductive substrate is selected from the group consisting of electrically conductive carbon, indium tin oxide, iridium oxide, nickel, platinum, silver, and gold.

5. The electrode sensor of claim 4, wherein said electrically conductive substrate is carbon.

6. The electrode sensor of claim 5, wherein said electrochemically active polymeric coating is a metallized or doped polymer.

7. The electrode sensor of claim 6, wherein said electrochemically active polymer coating is selected from the group consisting of metallized polymeric porphyrins, metallized polyphthalocyanines, polyvinylmetallocenes, metallized polyacetylenes, metallized polypyrrolines, and polymeric substituted glyoximes.

8. The electrode sensor of claim 7, wherein said electrochemically active polymeric coating is selected from the group consisting of metallized polymeric porphyrins and metallized polyphthalocyanines.

9. The electrode sensor of claim 8, wherein said electrochemically active polymeric coating is a metallized polymeric porphyrin which does not form metal-oxo bridges with said substrate.

10. The electrode sensor of claim 9, wherein said electrochemically active polymeric coating is selected from the group consisting of metallized polymeric pyrroles, pyridines, and ether porphyrins.

11. The electrode sensor of claim 10, wherein said electrochemically active polymeric coating is selected from the group consisting of metallized polymeric tetramethyl pyridine pyrrole and dimethyl ester porphyrins.

12. The electrode sensor of claim 11, wherein said electrochemically active polymeric coating is selected from the group consisting of polymeric tetramethyl pyridine pyrroles and dimethyl ester porphyrins metallized with $Ni^{2+}$, $Co^{2+}$, or $Fe^{3+}$.

13. The electrode sensor of claim 12, wherein said electrochemically active polymeric coating is $Ni^{2+}$ or $Fe^{3+}$ polymeric tetramethyl pyridine pyrrole.

14. The electrode sensor of claim 12, wherein said electrochemically active polymeric coating is $Fe^{3+}$ polymeric dimethyl ester porphyrin.

15. The electrode sensor of claim 12, which additionally comprises a gas-permeable membrane coating that is permeable to nitric oxide and is not permeable to nitrite.

16. A method of detecting nitric oxide in solution, which method comprises connecting an electrode sensor of claim 1 to a potentiostat, calibrating the potentiostat and electrode sensor for known concentrations of nitric oxide in solution, contacting said electrode sensor with an unknown sample, and detecting the presence or absence of nitric oxide in said unknown sample by comparing the measured current to a current for a sample of known nitric oxide concentration at a particular potential.

17. The method of claim 16, wherein said sample of known nitric oxide concentration has no nitric oxide.

18. The method of claim 16, wherein said the concentration of nitric oxide in said unknown sample is determined by comparing the measured current to currents observed for samples of more than one known nitric oxide concentration.

19. The method of claim 18, wherein said electrochemically active polymer coating of said electrode sensor is selected from the group consisting of polymeric tetramethyl pyridine pyrroles and dimethyl ester porphyrins metallized with $Ni^{2+}$, $Co^{2+}$, $Fe^{3+}$ and said electrically conductive substrate is carbon.

20. The method of claim 18, wherein said electrode sensor comprises a gas-permeable membrane coating that is permeable to nitric oxide and is not permeable to nitrite and said electrochemically active polymeric coating of said sensor is formed on the surface of said electrically conductive substrate by electrolytic polymerization.

21. The method of claim 18, wherein said electrode sensor comprises a gas-permeable membrane coating that is permeable to nitric oxide and is not permeable to nitrite and said electrochemically active polymeric coating of said sensor is formed on the surface of said electrically conductive substrate by electrolytic polymerization, and said electrochemically active polymer coating is selected from the group consisting of polymeric tetramethyl pyridine pyrroles and dimethyl ester porphyrins metallized with $Ni^{2+}$, $Co^{2+}$, or $Fe^{3+}$.

22. An electrode sensor for detecting the presence of NO in an analytic solution, the electrode sensor detecting an electrical signal developed between the electrode sensor and a counterelectrode, the electrode sensor comprising:

a) a conductive support having a catalytic surface for catalyzing NO oxidation and thereby generating a NO detection electrical signal; and b) a cationic exchanger disposed on the catalytic surface in contact with the analytic solution, the cationic exchanger allowing diffusion of NO therethrough but preventing the diffusion of anions to the catalytic surface that would mask the NO detection electrical signal.

23. The sensor of claim 22, wherein the conductive support having a catalytic surface comprises a conductive material with a layer of catalytic material disposed thereon.

24. The sensor of claim 23, wherein the cationic exchanger comprises a chemically stable perfluorosulfonic acid ion exchange resin.

25. The sensor of claim 23, wherein the catalytic material comprises a polymer selected from the group consisting of polymeric porphyrins, polypthalocyanines, polyvinylmethallocenes, polyacetylenes and polypyrrolines.

26. The sensor of claim 23, wherein the catalytic material comprises a carbon fiber.

27. The sensor of claim 23, wherein the catalytic material comprises a polymeric metalloporphyrin.

28. The sensor of claim 23, wherein the conductive material comprises tin indium oxide.

29. The sensor of claim 23, wherein the fiber is about 1 μm or less in diameter at one tip.

30. The sensor of claim 22, wherein the conductive material is a material selected from the group consisting of carbon, platinum and gold.

31. The sensor of claim 30, wherein the conductive material comprises platinum mesh.

32. A sensor system for measuring the level of NO in an analytic solution comprising:

a) an electrode sensor comprising a conductive support coated with a conductive layer of catalytic material that will catalyze NO oxidation and generate a detection signal, and a layer of cationic exchanger disposed on the catalytic material and making the detection signal selective to NO;

b) a counterelectrode; and c) an instrument for detecting an electrical signal developed between the electrode sensor and the counterelectrode in response to the oxidation of NO.

33. The sensor system of claim 32, wherein the conductive support comprises a conductive material and the catalytic material comprises a polymeric porphyrin.

34. The sensor system of claim 33, wherein the fiber of the electrode sensor comprises a carbon fiber, the counterelectrode comprises an inert conductive material and the reference electrode comprises a standard calomel electrode.

35. The sensor system of claim 33, wherein the conductive material comprises tin indium oxide.

36. The sensor system of claim 33, wherein the conductive material comprises platinum mesh.

37. The sensor system of claim 33, wherein the counterelectrode comprises a layer of tin indium oxide.

38. The sensor system of claim 32, further comprising:
   d) a reference electrode conductively connected to the measuring instrument.

39. A sensor for measuring the level of NO in an analytic solution comprising a conductive support coated with a plurality of layers of a polymeric metalloporphyrin for detecting oxides of nitrogen, and a coating of a cationic exchanger on the plurality of layers of metalloporphyrin, which cationic exchanger allows passage of NO but not anions of other nitrogen oxides and makes the sensor selective for NO.

40. The sensor of claim 39, wherein the conductive support comprises a conductive fiber having a tip diameter about 1 μm or less in diameter.

41. The sensor of claim 39, wherein the metalloporphyrin comprises tetrakis (3-methoxy-4-hydroxy-phenyl)porphyrin or meso-5'-0-P-phenylene-2',3'-0-isopropylidine uridinetri(n-methyl-4-pyridinium)porphyrin.

42. The sensor of claim 39, wherein the conductive support comprises inert metallic material.

43. The sensor of claim 42, wherein the conductive support comprises tin indium oxide.

44. The sensor of claim 42, wherein the cationic exchanger is a chemically stable perfluorosulfonic acid ion exchange resin.

45. The sensor of claim 42, wherein the conductive support comprises platinum.

46. An electrode sensor for a sensor for measuring the level of NO in an analytic solution, the sensor measuring an electrical signal developed between the electrode sensor and a counterelectrode, the electrode sensor comprising:
   a) a conductive support having a catalytic coating thereon comprising a polymeric metalloporphyrin layer disposed thereon for catalyzing NO oxidation, the oxidation developing an electrical signal at said electrode; and
   b) a cationic exchanger layer comprising a chemically stable perfluorosulfonic acid ion exchange resin disposed on the layer of catalytic material and in contact with the analytic solution which cationic exchanger layer prevents the diffusion of interfering anions to the catalytic layer surface, which interfering anions would adversely affect the NO oxidation electrical signal.

47. A method of manufacturing a nitric oxide-specific electrode sensor, which comprises contacting an electrically conductive substrate whose amperometric response is substantially unaffected by the presence of nitric oxide with a compound which forms an electrochemically active polymeric coating which interacts with NO to change the redox potential of NO and the electrode sensor.

48. The method of claim 47 wherein said electrochemically active polymeric coating is formed on the surface of said electrically conductive substrate by electrolytic polymerization.

49. The method of claim 48, wherein said electrically conductive substrate is selected from the group consisting of electrically conductive carbon, indium tin oxide, iridium oxide, nickel, platinum, silver, and gold.

50. The method of claim 49, wherein said electrochemically active polymeric coating is a metallized or doped polymer.

51. The method of claim 50, wherein said electrochemically active polymeric coating is selected from the group consisting of metallized polymeric porphyrins and metallized polyphthalocyanines.

52. The method of claim 51, wherein said electrically conductive substrate is carbon and said electrochemically active polymeric coating is selected from the group consisting of polymeric tetramethyl pyridine pyrroles and dimethyl ester porphyrins metallized with $Ni^{2+}$, $Co^{2+}$, or $Fe^{3+}$.

53. The method of claim 52, wherein said electrochemically active polymeric coating is $Ni^{2+}$ or $Fe^{3+}$ polymeric tetramethyl pyridine pyrrole.

54. The method of claim 52, wherein said electrochemically active polymeric coating is $Fe^{3+}$ polymeric dimethyl ester porphyrin.

55. The method of claim 52, which additionally comprises applying a coating of a gas-permeable membrane that is permeable to nitric oxide and excludes nitrite.

56. A method of directly measuring NO in an analytic solution generally comprising the steps of:
   a) providing an electrode sensor comprising a conductive support having a layer of catalytic material disposed thereon with a layer of a cationic exchanger disposed on the catalytic material;
   b) providing a counterelectrode;
   c) providing an instrument for measuring an electrical signal developed between the electrode sensor and the counterelectrode;
   d) placing the electrode sensor in the analytic solution;
   e) placing the counterelectrode in the analytic solution; and
   f) measuring the electrical signal developed between the electrode sensor and the counterelectrode.

57. The method of claim 56 further comprising the step of:
   g) providing a reference electrode; and
   h) placing the reference electrode in the analytic solution prior to measuring the electrical signal.

58. The method of directly measuring NO in an analytic solution as in claim 56, the provided electrode sensor being a microsensor in which the electrically conductive substrate is a glass carbon fiber having a tip approximately 1 μm or less in diameter, in which the electrochemically active polymeric coating is a metalloporphyrin selected from the group consisting of tetrakis (3-methoxy-4-hydroxyphenyl) porphyrin and meso-5'-0-P-phenylene-2',3'-0-isopropylidine uridine-tri(n-methyl-4-pyridinium)porphyrin, the porphyrin surface coverage (Γ) being in the approximate range of 0.7–1.2 nmol $cm^2$, and in which the cationic exchanger comprises a chemically stable perfluorosulfonic acid ion exchange resin disposed on the electrochemically active polymeric coating,
   the method conducted by a technique selected from the group consisting of differential pulse voltammetry and amperometry.

59. The method of claim 58, conducted by differential pulse voltammetry, with a pulse amplitude of approximately 40 mV, by obtaining differential pulse voltammograms for oxidation of NO at approximately 0.64 V;
   wherein a linear relationship is observed between current and NO concentration for a range of NO concentration from approximately zero up to approximately 300 μM NO concentration, with a detection limit calculated at a signal/noise ratio equal to 3 of approximately 20 nM, and with a detection in a volume of approximately $10^{-12}$ L of approximately $10^{-2}$ attomoles.

60. A nitric oxide-specific electrode sensor for detecting the quantity of NO in an analytic solution, the electrode sensor detecting an electrical signal developed between the electrode sensor and a counterelectrode, in strength in proportion to the quantity of NO in the analytic solution, the electrode sensor comprising:

(a) an electrically conductive substrate whose amperometric response is substantially unaffected by the presence of nitric oxide;

(b) an adherent and substantially uniform electrochemically active polymeric coating formed on a surface of said electrically conductive substrate, said electrochemically active polymeric coating interacting with NO in said analytical solution to change the redox potential of NO and the nitric oxide-specific electrode sensor, the change being in strength related to the quantity of NO in the analytic solution, and to generate an NO detection electrical signal in strength related to the quantity of NO in the analytic solution; and (c) a cationic exchanger disposed on a surface of said electrochemically active polymeric coating, the cationic exchanger being in contact with the analytic solution, the cationic exchanger allowing diffusion of NO therethrough but preventing the diffusion of anions to the surface of the electrochemically active polymeric coating that would mask the NO detection electrical signal; wherein the sensor may be used quantitatively to measure the levels of NO present in the analytic solution.

61. A nitric oxide-specific electrode sensor as in claim 60, the nitric oxide-specific electrode sensor being a microelectrode in which the electrically conductive substrate is a glass carbon fiber having a tip approximately 1 µm or less in diameter, in which the electrochemically active polymeric coating is a metalloporphyrin selected from the group consisting of tetrakis (3-methoxy-4-hydroxyphenyl) porphyrin and meso-5'-0-P-phenylene-2',3'-0-isopropylidine uridine-tri(n-methyl-4-pyridinium)porphyrin, the porphyrin surface coverage (Γ) being in the approximate range of 0.7–1.2 nmol $cm^2$, and in which the cationic exchanger comprises a chemically stable perfluorosulfonic acid ion exchange resin disposed on the electrochemically active polymeric coating.

62. The nitric oxide-specific electrode sensor of claim 61, the glass carbon fiber having a length in the range of approximately 4 µm to approximately 6 µm.

63. The nitric oxide-specific electrode sensor of claim 61, the electrode providing an NO detection electrical signal in aqueous analytic solutions having a pH of approximately 7.4.

64. The nitric oxide-specific electrode sensor of claim 60, the electrode providing an NO detection electrical signal in strength proportional to the quantity of NO in the analytic solution for NO concentrations in the approximate range of 20 to 60 µM.

65. A method of manufacturing a nitric oxidespecific electrode sensor, which comprises depositing a metalloporphyrin selected from among the group consisting of tetrakis (3-methoxy-4-hydroxyphenyl)porphyrin and meso-5'0-P-phenylene-2',3'-0-isopropylidine uridine-tri (n-methyl-4-pyridinium)porphyrin on an electrically conductive glass carbon fiber microelectrode having a tip approximately 1 µm or less in diameter, by electrolytic polymerization, to an average surface coverage (Γ) being in the approximate range of 0.7–1.2 nmol $cm^2$, to form an electrochemically active polymeric coating on the fiber which interacts with NO to change the redox potential of NO and the electrode sensor, and applying a coating on the metalloporphyrin of a cationic exchanger which comprises a chemically stable perfluorosulfonic acid ion exchange resin that is permeable to nitric oxide and exludes nitrite.

66. A method as in claim 65 further comprising depositing the metalloporphyrin from a solution of approximately 0.1M NaOH containing approximately $5\times10^{-4}$M monomeric tetrakis(3-methoxy-4-hydroxy-phenyl)porphyrin (TMHPP), with Ni as a central metal (TMHPPNi), by continuous scan cyclic voltammetry from approximately 0.0 to approximately 1.1 V, on the carbon fiber microelectrode, conditioning the resulting porphyrin film by multiple scans, storing the microelectrode in approximately 0.1M NaOH, and thereafter dipping the microelectrode in the cationic exchanger, drying the microelectrode, and storing the microelectrode in pH 7.4 buffer.

* * * * *